US006803376B1

(12) United States Patent
Appelbaum et al.

(10) Patent No.: US 6,803,376 B1
(45) Date of Patent: Oct. 12, 2004

(54) METHOD OF USE OF QUINOLONE COMPOUNDS AGAINST PNEUMOCOCCAL AND HAEMOPHILUS BACTERIA

(75) Inventors: Peter C. Appelbaum; Kim L. Credito; Todd Davies; Diane B. Hoellman; Linda M. Kelly; Glenn A. Pankuch, all of Hershey, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/569,648

(22) Filed: May 12, 2000

Related U.S. Application Data

(63) Continuation-in-part of application No. 09/399,657, filed on Sep. 21, 1999, now abandoned
(60) Provisional application No. 60/141,456, filed on Jun. 29, 1999, provisional application No. 60/142,729, filed on Jul. 8, 1999, and provisional application No. 60/142,725, filed on Jul. 8, 1999.

(51) Int. Cl.$^7$ ............................................. A61K 31/47
(52) U.S. Cl. ................................... 514/311; 514/312
(58) Field of Search ................................ 514/311, 312

(56) References Cited

U.S. PATENT DOCUMENTS

| | | | |
|---|---|---|---|
| 5,633,262 A | 5/1997 | Hong et al. | 514/300 |
| 5,776,944 A | 7/1998 | Hong et al. | 516/300 |
| 5,869,670 A | 2/1999 | Hong et al. | 546/123 |
| 5,962,468 A | 10/1999 | Hong et al. | 514/300 |

FOREIGN PATENT DOCUMENTS

| | | |
|---|---|---|
| EP | 0 688 772 A1 | 12/1995 |
| WO | WO 98/42705 | 10/1998 |
| WO | WO 00/24932 | 5/2000 |

OTHER PUBLICATIONS

J-I. Oh et al., "In vitro and In vivo Antibacterial Activities of LB20304, a New fluoronaphthyridone," *Abstracts of the 35th ICAAC*, p. 148, S-122, Abst F205 (1995).

Y-K. Kim et al., "Synthesis and Antibacterial Activities of LB20304: A New Fluoronaphthyridone Antibiotic Containing Novel Oxime Functionalized Pyrrolidine," *Abstracts of the 35th ICAAC*, p. 148, S-122, Abst F204 (1995).

Spangler, et al., "Postantibiotic Effect of Sanfetrinem Compared with Those of Six Other Agents against 12 Penicillin-Susceptible and—Resistant Pneumococci," *Antimicrobial Agents and Chemotherapy*, 41(10): 2173-2176 (1997).

Pankuch, et al., "Study of Comparative Antipneumoccal Activities of Penicillin G, RP 59500, Erythromycin, Sparfloxacin, Ciprofloxacin, and Vancomycin by Using Time-Kill Methodology," *Antimicrobial Agents and Chemotherapy*, 38(9): 2065-2072(1994).

Licata, et al., "Comparison of the Postantibiotic and Postantibiotic Sub-MIC Effects of Levofloxacin and Ciprofloxacin on *Staphylococcus aureus* and *Streptococcus pneumoniae*," *Antimicrobial Agents and Chemotherapy*, 41(5): 950-955 (1997).

Pankuch, et al., "Comparative activity of ampicillin, amoxycillin, amoxycillin/clavulanate and cefotaxime against 189 penicillin-susceptible and -resistant pneumococci." *Journal of Antimicrobial Chemotherapy*, 35: 883-885 (1995).

Spangler, et al., "Susceptibility of 170 penicillin-susceptible and penicillin-resistant pneumococci to six oral cephalosporins, four quinolones, desacetylcefotaxime, Ro 23-9424 and RP 67829," *Journal of Antimicrobial Chemotherapy*, 31: 273-280 (1993).

Jacobs, "Treatment and Diagnosis of Infections Caused by Drug-Resistant *Streptococcus pneumoniae*," *Clinical Infectious Disease*, 15: 119-127 (1992).

Munoz, et al., "Geographic Distribution of Penicillin-Resistant Clones of *Streptococcus pneumoniae*: Characterization by Penicillin-Binding Protein Profile, Surgace Protein A Typing, and Multilocus Enzyme Analysis," *Clinical Infectious Diseases*, 15: 112-118 (1992).

Friedland, et al., "Management of Infectious Caused by Antibiotic-Resistant *Streptococcus pneumoniae*," *New England Journal of Medicine*, 331(6): 377-382 (1994).

Pankuch, et al., "Antipneumococcal Activities of RP59500 (Quinupristin-Dalfopristin) Penicillin G, Erythromycin, and Sparfloxacin Determined by MIC and Rapid Time-Kill Methodologies," *Antimicrobial Agents and Chemotherapy*, 40(7): 1653-1656 (1996).

Appelbaum, "Antimicrobial Resistance in *Streptococcus pneumoniae*: An Overview," *Clinical Infectious Diseases*, 15: 77-83 (1992).

Oh, et al., "In Vitro and In Vivo Evaluations of LB20304, a New Fluoronaphthyridone," *Antimicrobial Agents and Chemotherapy*, 40(6): 1564-1568 (1996).

Block, et al., "Penicillin-resistant *Streptococcus pneumoniae* in acute otitis media: risk factors, susceptibility patterns and antimicrobial management," *Pediatric Infectious Diseases*, 14(9): 751-759 (1995).

Friedland, et al., "Management of penicillin-resistant pneumococcal infections," *Pediatric Infectious Diseases*, 11(6): 433-435 (1992).

(List continued on next page.)

*Primary Examiner*—Kevin E. Weddington
(74) *Attorney, Agent, or Firm*—Loretta J. Henderson; Mary E. McCarthy; Charles M. Kinzig

(57) ABSTRACT

This invention relates, in part, to newly identified methods of using quinolone antibiotics, particularly a gemifloxacin compound against certain pathogenic bacteria, particularly quinolone resistant *S. pnemoniae* and rare *H. influenzae* strains.

34 Claims, No Drawings

OTHER PUBLICATIONS

Pan, et al., "Involvement of Topoisomerase IV and DNA Gyrase as Ciprofloxacin Targets in *Streptococcul pneumoniae*," *Antimicrobial Agents and Chemotheray*, 40(10): 2321–2326 (1996).

Visalli, et al., "MIC and Time–Kill Study of Activities of DU–6859a, Ciprofloxacin, Levofloxacin, Sparfloxaci, Cefotaxime, Imipenem, and Vancomycin against Nine Penicillin–Susceptible and –Resistant Pneumococci," *Antimicrobial Agents and Chemotherapy*, 40(2): 362–366 (1996).

Spangler, et al., "Postantibiotic Effect and Postantibiotic Sub–MI Effect of Levofloxacin Compared to Those of Ofloxacin, Ciprofloxacin, Erythromycin, Azithromycin, and Clarithromycin against 20 Pneumococci," *Antimicrobial Agents and Chemotherapy*, 42(5): 1253–1255 (1998).

Brenwald, et al, "Prevalence of a Putative Efflux mechanism among Fluoroquinolone–Resistant. Clinical Isolates of *Streptococcus pneumoniae*," *Antimicrobial Agents and Chemotherapy*, 42(8): 2032–2035 (1998).

McDougal, et al., "Analysis of Multiply Antimicrobial–Resistant Isolates of *Streptococcus pneumoniae*," *Antimicrobial Agents and Chemotherapy*, 36(10): 2176–2184 (1992).

Doern, et al., "Antimicrobial Resistance of *Streptococcus pneumoniae* Recovered from Outpatients in the United States during the Winter Months of 1994 to 1995: Results of a 30–Center National Surveillance Study," *Antimicrobial Agents and Chemotherapy*, 40(5): 1208–1213 (1996).

Fuursted, et al., "Comparative Study of Bactericidal Activities, Postantibiotic Effects, and Effects on Bacterial Virulence of Penicillin G and Six Macroslides against *Streptococcus pneumoniae*," *Antimicrobial Agents and Chemotherapy*, 41(4): 781–784 (1997).

Davies, et al., "In Vitro Development of Resistance of Five Quinolones and Amoxicillin–Clavulanate in *Streptococcus pneumoniae*," *Antimicrobial Agents and Chemotherapy*, 43(5): 1177–1182 (1999).

Cormican, et al., "Antimicrobial Activity and Spectrum of LB20304, a Novel Fluoronaphthyridone," *Antimicrobial Agents and Chemotherapy*, 41(1): 204–211 (1997).

Jacobs, et al., "Antibiotic–resistant pneumococci," *Review in Medical Microbiology*, 6(2): 77–93 (1995).

Hohl, et al., "International multicenter investigation of LB20304, a new flurornaphthyridone," *Clinical Microbiology and Infections*, 4: 280–284 (1998).

Jorgensen, et al., "Methods for Dilution Antimicrobial Susceptibility Tests for Bacterial That Grow Aerobically," *NCCLS*, 3rd ed.: 1–86 (1997).

Craig, et al., "Postantibiotic Effect," *Antibiotics in Laboratory Medicine*, 4th ed.: 296–329 (1996).

Kelly, et al. "SB–265805: A Potent New Quinolone," *ICAAC*, San Diego Convention Centre, 105–F Poster Session: 1–41 (1998).

Georgiou, et al., "Ciprofloxacin–Resistant *Haemophilus influenzae* Strains Process Mutations in Analogous Positions of GyrA and ParC," *Antimicrobial Agents and Chemotherapy*, 40(7): 1741–1744, (1996).

Vila, et al., "Increase in Quinolone Resistance in a *Haemophilus influenzae* Strain Isolated from a Patient with Recurrent Respiratory Infections Treated with Ofloxacin," *Antimicrobial Agents and Chemotherapy*, 43(1): 161–162 (1999).

Zeckel, et al., "Loracarbef (LY163892) Versus Amoxicillin/Clavulanate in the Treatment of Acute Bacterial Exacerbations of Chronic Bronchitis," *Clinical Therapeutics*, 14(2): 214–229 (1992).

Fang, et al., "New and Emerging Etiologies for Community–Acquired Pneumonia with Implications for Therapy," *Medicine*, 69(5): 307–316 (1990).

Jacobs, et al., "Susceptibilities of *Streptococcus pneumoniae* and *Haemophilus inflenzae* to 10 Oral Antimicrobial Agents Based on Pharmacodynamic Parameters: 1997 U.S. Surveillance Study," *Antimicrobial Agents and Chemotherapy*, 43(8): 1901–1908 (1999).

Hoberman, et al., "Efficacy of amoxicillin/clavulanate for acute otitis media: relation to *Streptococcus pneumoniae* susceptibility," *Pediatric Infectious Disease Journal*, 15(10): 955–962 (1996).

Bootsma, et al., "Isolation and characterization of a ciprofloxacin–resistant isolate of *Haemophilus influenzae* from The Netherlands," *Journal of Antimicrobial Chemotherapy*, 39: 292–293 (1997).

Jorgensen, et al., "Methods for Dilution Antimicrobial Susceptibility Tests for Bacteria That Grow Aerobically," *Natl. Comm. for Clin. Lab. Standards*, 17(2): M7–A4, 1–27 (1997).

Spangler, et al., "Susceptibilities of Penicillin–Susceptible and –Resistant Strains of *Streptococcus pneumoniae* to RP59500, Vancomycin, Erythromycin, PD 131628, Sparfloxacin, Temafloxacin, Win 57272, Ofloxacin, and Cirpofloxacin," *Antimicrobial Agents and Chemotherapy*, 36(4): 856–859 (1992).

Pankuch, et al., "Activity of CP99.219 compared with Du–6859a, ciprofloxacin, ofloxacin, levofloxacin, lomefloxacin, tosufloxacin, sparfloxacin and grapafloxacin against penicillin–susceptible and–resistant pneumococci," *Journal of Antimicrobial Chemotherapy*, 35: 230–232 (1995).

Breiman, et al., "Emergence of Drug–Resistant Pneumococcal Infections in the United States," *JAMA*, 271(23): 1831–1835 (1994).

G. Cormican, "Comparative Antimicrobial and Spectrum Activity of LB20304a, a New Fluoronated Naphthyridone Compound", *Abstracts of the 36th ICAAC*, 109 Abst F53 (1996).

J–H. Kwak, "Antimicrobial Activities of LB20304a, a New Quinolone Antibiotic", *The Journal of Applied Pharmacology* (4) pp. 378–384 (1996).

M–K. Seo, "Pharmacokinetics of LB20304, a New Fluoroquinolone, in Rats and Dogs", *Arch. Pharm. Res.* vol. 19, No. 5, pp. 359–367 (1996).

C. Yong Hong, et al., "Novel Fluoroquinolone Antibacterial Agents Containing Oxime–Substituted (Aminomethyl) pyrrolidines: Synthesis and Antibacterial Activity of 7–(4–(Aminomethyl)–3–(methoxyimino) pyrrolidin–1–yl)–1–cyclopropyl–6–fluoro–4–oxo–1,4–dihydro [1,8] naphthyridine–3–carboxylic Acid (LB20304)", *J. Med. Chem.* 40 (22) pp. 3584–3593 (1997).

M–K. Seo et al., "High Performance Liquid Chromatographic Assay of a New Fluoroquinolone, LB20304, in the Plasma of Rats and Dogs", *Arch. Pharm. Res.* vol. 19, No. 6, pp. 554–558 (1996).

M–J. Ahn, et al., "In Vivo Efficacy of LB20304a against Experimental Respiratory Tract Infection in Mice", *Yakhak Hoeji* vol. 40, No. 4, pp. 438–441 (1996).

M–J. Ahn, et al., "Effects of a New Fluoroquinolone LB20304a on Microflora of Caecum in Mice", *Yakhak Hoeji* vol. 40, No. 3, pp. 343–346 (1996).

K–S. Paek, et al., "Factors Affecting In Vitro Activity of LB20304, New Fluoroquinolone", *Arch. Pharm. Res.* vol. 19, No. 2, pp. 143–147 (1996).

M–J. Ahn, et al, "Post–Antibiotic Effect of LB20304, A New Quinolone Antibiotic", *Yakhak Hoeji* vol. 40, No. 3, pp. 347–350 (1996).

F. Marco, et al., "Antimicrobial Activity of LB20304, a Fluoronaphthyridone, Tested Against Anaerobic Bacteria", *J. Antimicrobial Chemother* vol. 40, No. 4, pp. 605–607 (1997).

K–S. Paek, et al, "Bactericidal Activities of LB20304, a New Fluoroquinolone", *Arch. Pharm. Res.* vol. 19, No. 4, pp. 317–320 (1996).

M. Kim, et al, "In Vitro Activities of LB20304, a New Fluoroquinolone", *Arch. Pharm. Res.* vol. 19, No. 1, pp. 52–59 (1996).

M–Y. Kim, et al, Bacterial Resistance to LB20304, a New Fluoroquinolone Antibiotic, *Arch. Pharm. Res.* vol. 19, No. 5, pp. 400–405 (1996).

Kelly et al., "Antipneumococcal Activity of SB 265805 (A New Broad Spectrum Quinolone) Compared with Nine Compounds by MIC," 38th ICAAC, San Diego CA, Abst F–87, p. 254 (1998).

U.S. application No. 09/577,732, filed May 23, 2000, Methods of Use of Gemifloxacin Compounds Against Fluoroquinolone Resistant *Streptococcus Pneumoniae* Bacteria.

U.S application No. 09/577,731, Bast et al., filed May 23, 2000, Methods of Use of Gemifloxacin Compounds Against Fluoroquinolone Resistant *Streptococcus Pneumoniae* Bacteria.

U.S. application No. 09/611,998, Appelbaum et al., filed Jul. 7, 2000, Methods of Use of Fluoroquinolone Compounds Against Ciprofloxacin–Resistant And Ciprofloxacin–Sensitive Pathogenic Bacteria.

U.S. application No. 09/395,492, Dubois et al., filed Mar. 23, 2001, Methods of Use of Fluoroquinolone Compounds Against Maxillary Sinus Pathogenic Bacteria.

U.S. application No. 09/399,855, Crabb et al., filed Sep. 21, 1999, Methods of Use of Antimicrobial Compounds Against Pathogenic Mycoplasma Bacteria.

Tankovic et al., Contribution of Mutations in gyrA and parC genes to fluoroquinolone resistance of mutants of streptococcus pneumoniae obtained in vivo and in vitro, Antimicrobial Agents and Chemotherapy, Nov. 1996, 2505–2510.

Munoz et al, ParC subunit of DNA topoisomerase IV of streptococcus pneumoniae is a primary target of fluoroquinolones and cooperate with DNA gyrase A subunit in forming resistance phenotype, Antimicrobial Agents and Chemotherapy, Oct. 1996, 2252–2257.

Janoir et al, High–level fluoroquinolone resistance in streptococcus pneumoniae requires mutations in parC and gyr A, Antimicrobial Agents and Chemotherapy, Dec. 1996, 2760–2764.

Pan et al., targeting of DNA gyrase in streptococcus pneumoniae by sparfloxacin: selective targeting of gyrase or topoisomerase IV by quinolones, Antimicrobial Agents and Chemotherapy, Feb. 1996, 471–474.

Perichon et al., characterization of a mutation in the parE gene that confers fluoroquinolone resistance in streptococcus pneumoniae, Antimicrobial Agents and Chemotherapy, May 1997, 1166–1167.

Baranova et al., apparent involvement of a multidrug transporter in the fluoroquinolone resistance of streptococcus pneumoniae, Antimicrobial Agents and Chemotherapy, Jun. 1997, 1396–1398.

Zeller et al., active efflux as a mechanism of resistance to ciprofloxacin in streptococcus pneumoniae, Antimicrobial Agents and Chemotherapy, Sep. 1997, 1973–1978.

Gonzalez et al., fluoroquinoone resistance mutations in the parC, parE, and gyrA genes of clinical isolates of viridans group streptococci, Antimicrobial Agents and Chemoherapy, Nov. 1998, 2792–2798.

Pan et al., DNA gyrase topoisomerase IV are dual targets of clinafloxacin action in streptococcus pneumoniae, Antimicrobial Agents and Chemotherapy, Nov. 1998, 2810–2816.

Piddock et al., activities of new fluoroquinolones against fluoroquinolone–resistant pathogens of the lower respiratory tact, Antimicrobial Agents and Chemotherapy, Nov. 1998, 2956–2960.

Gill et al., identification of an efflux pump gene, pmrA, associated with fluoroquinolone resistance in streptococcus pneumoniae, Antimicrobial Agents and Chemotherapy, Jan. 1999, 187–189.

Brenwald et al., the effect of reserpine, an inhibitor of multi–drug efflux pumps, on the in–vitro susceptibilities of fluoroquinolone–resistant strains of streptococcus pneumoniae to norfloxacin, J. Antimicrob Chemother 1997, 40, 458–460.

METHOD OF USE OF QUINOLONE COMPOUNDS AGAINST PNEUMOCOCCAL AND HAEMOPHILUS BACTERIA

This application is a Continuation-in-Part to U.S. application Ser. No. 09/399,657, filed Sep. 21, 1999, now abandoned U.S. Provisional Application Nos. 60/141,456, filed Jun. 29, 1999, 60/142,749 filed Jul. 8, 1999 and 60/142,725, filed Jul. 8, 1999. This invention relates, in part, to newly identified methods of using quinolone antibiotics, particularly a gemifloxacin compound against pneumococcal and *Haemophilus influenzae* bacteria, such as *Streptococcus pneumoniae*, particularly quinolone-resistant strains, and Haemophilus strains, particularly rare strains of *Haemophilus influenzae*.

BACKGROUND OF THE INVENTION

Quinolones have been shown to be effective to varying degrees against a range of bacterial pathogens. However, as diseases caused by these pathogens are on the rise, there exists a need for antimicrobial compounds that are more potent than the present group of quinolones.

Gemifloxacin mesylate (SB-265805) is a novel fluoroquinolone useful as a potent antibacterial agent. Gemifloxacin compounds are described in detail in patent application PCT/KR98/00051 published as WO 98/42705. Patent application EP 688772 discloses novel quinolone(naphthyridine) carboxylic acid derivatives, including anhydrous (R,S)-7-(3-aminomethyl-4-methoxyiminopyrrolidin-1-yl)-1-cyclopropyl-6-fluoro-4-oxo-1,4-dihydro-1,8-naphthyridine-3-carboxylic acid of formula I.

STRUCTURE I

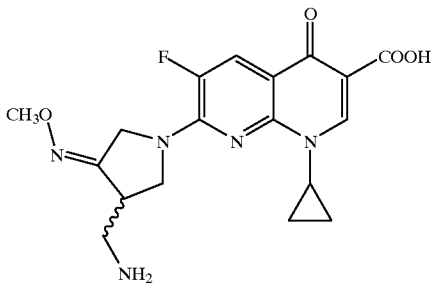

PCT/KR98/00051 discloses (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate and hydrates thereof including the sesquihydrate.

I. Pneumococcal Pathogens

The incidence of pneumococci resistant to penicillin G and other β-lactam and non-β-lactam compounds has increased worldwide at an alarming rate, including in the U.S. Major foci of infections currently include South Africa, Spain, Central and Eastern Europe, and parts of Asia (P. C. Appelbaum, *Clin. Infect. Dis.* 15:77–83, 1992; Friedland, et al., *Pediatr. Infect. Dis.* 11:433–435, 1992; Friedland, et al., *N. Engl. J. Med.* 331:377–382, 1994; Jacobs, et al., *Clin. Infect. Dis.* 15:119–127, 1992 and Jacobs, et al., *Rev. Med. Microbiol.* 6:77–93, 1995). In the U.S. a recent survey has shown an increase in resistance to penicillin from <5% before 1989 (including <0.02% of isolates with MICs ≧2.0 μg/ml) to 6.6% in 1991–1992 (with 1.3% of isolates with MICs ≧2.0 μg/ml) (Brieman, et al., *J. Am. Med. Assoc.* 271:1831–1835, 1994). In another more recent survey, 23.6% (360) of 1527 clinically significant pneumococcal isolates were not susceptible to penicillin (Doern, et al., *Antimicrob. Agents Chemother.* 40:1208–1213, 1996). It is also important to note the high rates of isolation of penicillin intermediate and resistant pneumococci (approximately 30%) in middle ear fluids from patients with refractory otitis media, compared to other isolation sites (Block, et al., *Pediatr. Infect. Dis.* 14:751–759, 1995). The problem of drug-resistant pneumococci is compounded by the ability of resistant clones to spread from country to country, and from continent to continent (McDougal, et al., *Antimicrob. Agents Chemother.* 36:2176–2184, 1992; Munoz, et al., *Clin. Infect. Dis.* 15:112–118, 1992).

There is an urgent need of oral compounds for out-patient treatment of otitis media and respiratory tract infections caused by penicillin intermediate and resistant pneumococci (Friedland, et al., *Pediatr. Infect. Dis.* 11:433–435, 1992; Friedland, et al., *N. Engl. J. Med.* 331:377–382, 1994; M. R. Jacobs, *Clin. Infect. Dis.* 15:119–127, 1992; and Jacobs, et al., *Rev. Med. Microbiol.* 6:77–93, 1995). Available quinolones such as ciprofloxacin and ofloxacin yield moderate in vitro activity against pneumococci, with MICs clustering around the breakpoints (Spangler, et al., *Antimicrob. Agents Chemother.* 36:856–859, 1992; and Spangler, et al., *J. Antimicrob. Chemother.* 31:273–280, 1993). Gemifloxacin (SB 265805)(LB 20304a) is a new broad-spectrum fluoronaphthyridone carboxylic acid with a novel pyrrolidone substituent (Cormican, et al., *Antimicrob. Agents Chemother.* 41:204–211, 1997; Hohl, et al., *Clin. Microbiol. Infect.* 4:280–284, 1998; and Oh, et al., *Antimicrob. Agents Chemother.* 40:1564–1568, 1996). Previous preliminary studies (Cormican, et al., *Antimicrob. Agents Chemother.* 41:204–211, 1997; Hohl, et al., *Clin. Microbiol. Infect.* 4:280–284, 1998; and Oh, et al., *Antimicrob. Agents Chemother.* 40:1564–1568, 1996) have shown that this compound is very active against pneumococci. This study further examined the antipneumococcal activity of gemifloxacin compared to ciprofloxacin, levofloxacin, sparfloxacin, grepafloxacin, trovafloxacin, amoxicillin, cefuroxime, azithromycin and clarithromycin by i) agar dilution testing of 234 quinolone susceptible and resistant strains; ii) examination of resistance mechanisms in quinolone resistant strains; iii) time-kill testing of 12 strains; iv) examination of the post-antibiotic effect (herein "PAE") of drugs against 6 strains.

Provided herein is a significant discovery made using a gemifloxacin compound against a range of penicillin susceptible and resistant pneumococci by agar dilution, microdilution, time-kill and post-antibiotic effect methodology. Against 64 penicillin susceptible, 68 intermediate and 75 resistant pneumococci (all quinolone susceptible), agar dilution $MIC_{50/90}$ values (μg/ml) were as follows: gemifloxacin, 0.03/0.06; ciprofloxacin, 1.0/4.0; levofloxacin, 1.0/2.0; sparfloxacin, 0.5/0.5; grepafloxacin, 0.125/0.5; trovafloxacin, 0.125/0.25; amoxicillin, 0.016/0.06 (penicillin susceptible), 0.125/1.0 (penicillin intermediate), 2.0/4.0 (penicillin resistant); cefuroxime, 0.03/0.25 (penicillin susceptible), 0.5/2.0 (penicillin intermediate), 8.0/16.0 (penicillin resistant); azithromycin, 0.125/0.5 (penicillin susceptible), 0.125/>128.0 (penicillin intermediate), 4.0/>128.0 (penicillin resistant); clarithromycin, 0.03/0.06 (penicillin susceptible), 0.03/32.0 (penicillin intermediate), 2.0/>128.0 (penicillin resistant). Against 28 strains with ciprofloxacin MICs ≧8 μg/ml, gemifloxacin had the lowest MICs (0.03–1.0 μg/ml, $MIC_{90}$ 0.5 μg/ml), compared with MICs ranging between 0.25 to >32.0 µg/ml)(MIC$_{90}$s 4.0→32.0 µg/ml) for the other quinolones. Resistance in these 28 strains was associated with mutations in parC, gyrA, parE, and/or gyrb or efflux, with some strains having multiple resistance mechanisms. For 12 penicillin susceptible and resistant pneumococcal strains (2 quinolone resistant), time-kill results showed that levofloxacin at the MIC, gemifloxacin and sparfloxacin at 2×MIC and ciprofloxacin, grepafloxacin and trovafloxacin at 4×MIC, were bactericidal after 24 h. Gemifloxacin was uniformly bactericidal after 24 h at ≦0.5 µg/ml. Various degrees of 90% and 99% killing by all quinolones was detected after 3 h. Gemifloxacin and trovafloxacin were both bactericidal at the microbroth MIC for the two quinolone resistant pneumococcal strains. Amoxicillin, at 2×MIC and cefuroxime at 4×MIC, were bactericidal after 24 h, with some degree of killing at earlier time periods. By contrast, macrolides gave slower killing against the 7 susceptible strains tested, with 99.9% killing of all strains at 2–4×MIC after 24 h. Post-antibiotic effects for 5 quinolone susceptible strains were similar (0.3–3.0 h) for all quinolones tested, and significant quinolone PAEs were found for the quinolone-resistant strain.

Also provided herein is a significant discovery made using a gemifloxacin compound against quinolone-resistant pneumococci, demonstrating the activity of the gemifloxacin compound used was superior to a number of quinolones as described in more detail herein. Gemifloxacin compounds are valuable compounds for the treatment of infections caused by a range of pneumococcal pathogens, including those resistant to usual oral therapy, thereby filling an unmet medical need.

II. Haemophilus Pathogens

Although development of an effective vaccine against *Haemophilus influenzae* type b has led to disappearance of this organism in many parts of the world, its place has been taken by untypeable *H. influenzae* strains. The latter organisms (followed by *Streptococcus pneumoniae* and *Moraxella catarrhalis*) are now considered to be the leading cause of acute exacerbations of chronic bronchitis, and an important cause, together with *S. pneumoniae* and *M. catarrhalis*, of acute otitis media, sinusitis and conmmunity-acquired respiratory tract infections (Fang, et al., *Medicine (Baltimore)* 69:307–316, 1990; Hoberman, et al., *Pediatr. Infect. Dis.* 10:955–962, 1996; Jacobs, et al., *Antimicrob. Agents Chemother*, In press; and Zeckel, et al., *Clin. Ther.* 14:214–229, 1992).

Current recommendations by the NCCLS for use of Haemophilus Test Medium (herein "HTM") for Haemophilus susceptibility testing have been complicated by difficulty in commercial manufacture of this medium, and its short balf-life when made in-house. Reliable Haemophilus susceptibility testing with HEM requires use of freshly made medium used within 3 weeks of making (Methods for Dilution Antimicrobial Susceptibility Tests for Bacteria that Grow Aerobically, 3rd Edition, NCCLS, Wayne, Pa., 1997).

Previous preliminary studies have shown that this gemifloxaxin is very active against Haemophilus and Moraxella (Cormican, et al., *Antimicrob. Agents Chemother.* 41:204–211, 1997; Hohl, et al., *Clin. Microbiol. Infect.* 4:280–284, 1998; and Oh, et al., *Antimicrobial Agents Chemother.* 40:1564–1568, 1996).

A further embodiment provided herein is based in part on a significant discovery made using a gemifloxacin compound against nine rare clinical strains of *Haemophilus influenzae* from Europe with increased ciprofloxacin MICs were tested for in vitro activity (MICs) of gemifloxacin (SB-265805), ciprofloxacin, levofloxacin, sparfloxacin, grepafloxacin and trovafloxacin and checked for mutations in gyrA, parC, gyrB and parE, demonstrating the activity of the gemifloxacin compound used was superior to a number of quinolones as described in more detail herein. Gemifloxacin compounds are valuable compounds for the treatment of infections caused by a range of *Haemophilus influenzae* strains, including those resistant to usual oral therapy, thereby filling an unmet medical need.

SUMMARY OF THE INVENTION

I. Pneumococcal Pathogens

An object of the invention is a method for modulating metabolism of pneumococcal pathogenic bacteria comprising the step of contacting pneumococcal pathogenic bacteria with an antibacterially effective amount of a composition comprising a quinolone, particularly a gemifloxacin compound, or an antibacterially effective derivative thereof.

A further object of the invention is a method wherein said pneumococcal pathogenic bacteria is selected from the group consisting of: bacteria comprising a mutation in a quinolone resistance-determining region (QRDR) of parC, gyrA, parE, and/or gyrb; bacteria comprising a mutation in ParC at S79-F or Y, D83-N, R95-C, or K137-N; bacteria comprising a mutation in gyrA at S83-A, C, F, or Y; E87-K; or S116-G; bacteria comprising a mutation in parE at D435-N or I460-V; bacteria comprising a mutation in gyrB at D435-N or E474-K; bacteria comprising at least four mutations in a QRDR or parC, gyrA, parE, and gyrB; bacteria comprising a mutation in a quinolone resistance-determining region (QRDR) of parC, gyrA, parE, and/or gyrB; bacteria that are ciprofloxacin-resistant, levofloxacin-resistant, sparfloxacin-resistant, grepafloxacin-resistant, or trovafloxacin-resistant, or a combination thereof, that comprise a mutation in ParC at S79-F or Y, D83-N, R95-C, or K137-N; bacteria that are ciprofloxacin-resistant, levofloxacin-resistant, sparfloxacin-resistant, grepafloxacin-resistant, or trovafloxacin-resistant, or a combination thereof, that comprise a mutation in gyrA at S83-A, C, F, or Y; E87-K; or S116-G; bacteria that are ciprofloxacin-resistant, levofloxacin-resistant, sparfloxacin-resistant, grepafloxacin-resistant, or trovafloxacin-resistant, or a combination thereof, that comprise a mutation in parE at D435-N or I460-V; bacteria that are ciprofloxacin-resistant, levofloxacin-resistant, sparfloxacin-resistant, grepafloxacin-resistant, or trovafloxacin-resistant, or a combination thereof, that comprise a mutation in gyrB at D435-N or E474-K; bacteria that are ciprofloxacin-resistant, levofloxacin-resistant, sparfloxacin-resistant, grepafloxacin-resistant, or trovafloxacin-resistant, or a combination thereof, that comprise at least four mutations in a QRDR or parC, gyrA, parE, and gyrB; bacteria that are ciprofloxacin-resistant, levofloxacin-resistant, sparfloxacin-resistant, grepafloxacin-resistant, or trovafloxacin-resistant, or a combination thereof, that comprise a mutation in a quinolone resistance-determining region (QRDR) of parC, gyrA, parE, and/or gyrB; *Streptococcus pneumoniae* bacteria comprising a mutation in ParC at S79-F or Y, D83-N, R95-C, or K137-N; *Streptococcus pneumoniae* bacteria comprising a mutation in gyrA at S83-A, C, F, or Y; E87-K; or S116G; *Streptococcus pneumoniae* bacteria comprising a mutation in pare at D435-N or I460-V; *Streptococcus pneumoniae* bacteria comprising a mutation in gyrB at D435-N or E474-K; *Streptococcus pneumoniae* bacteria comprising at least four mutations in a QRDR or parC, gyrA, parE, and gyrB; and *Streptococcus pneumoniae* bacteria comprising a mutation in a quinolone resistance-determining region (QRDR) of parC, gyrA, parE, and/or gyrB.

Also provided by the invention is a method of treating or preventing a bacterial infection by pneumococcal pathogenic bacteria comprising the step of administering an antibacterially effective amount of a composition comprising a quinolone, particularly a gemifloxacin compound to a mammal suspected of having or being at risk of having an infection with pneumococcal pathogenic bacteria.

A preferred method is provided wherein said modulating metabolism is inhibiting growth of said bacteria or killing said bacteria.

A further preferred method is provided wherein said contacting said bacteria comprises the further step of introducing said composition into a mammal, particularly a human.

Further preferred methods are provided by the invention wherein said bacteria is selected from the group consisting of: bacteria comprising a mutation in a quinolone resistance-determining region (QRDR) of parC, gyrA, parE, and/or gyrB; bacteria comprising a mutation in ParC at S79-F or Y, D83-N, R95-C, or K137-N; bacteria comprising a mutation in gyrA at S83-A, C, F, or Y; E87-K; or S116-G; bacteria comprising a mutation in parE at D435-N or I460-V; bacteria comprising a mutation in gyrB at D435-N or E474-K; bacteria comprising at least four mutations in a QRDR or parC, gyrA, parE, and gyrB; bacteria comprising a mutation in a quinolone resistance-determining region (QRDR) of parC, gyrA, parE, and/or gyrB; bacteria that are ciprofloxacin-resistant, levofloxacin-resistant, sparfloxacin-resistant, grepafloxacin-resistant, or trovafloxacin-resistant, or a combination thereof, that comprise a mutation in ParC at S79-F or Y, D83-N, R95-C, or K137-N; bacteria that are ciprofloxacin-resistant, levofloxacin-resistant, sparfloxacin-resistant, grepafloxacin-resistant, or trovafloxacin-resistant, or a combination thereof, that comprise a mutation in gyrA at S83-A, C, F, or Y; E87-K; or S116-G; bacteria that are ciprofloxacin-resistant, levofloxacin-resistant, sparfloxacin-resistant, grepafloxacin-resistant, or trovafloxacin-resistant, or a combination thereof, that comprise a mutation in pare at D435-N or I460-V; bacteria that are ciprofloxacin-resistant, levofloxacin-resistant, sparfloxacin-resistant, grepafloxacin-resistant, or trovafloxacin-resistant, or a combination thereof, that comprise a mutation in gyrB at D435-N or E474-K; bacteria that are ciprofloxacin-resistant, levofloxacin-resistant, sparfloxacin-resistant, grepafloxacin-resistant, or trovafloxacin-resistant, or a combination thereof, that comprise at least four mutations in a QRDR or parC, gyrA, parE, and gyrB; bacteria that are ciprofloxacin-resistant, levofloxacin-resistant, sparfloxacin-resistant, grepafloxacin-resistant, or trovafloxacin-resistant, or a combination thereof, that comprise a mutation in a quinolone resistance determining region (QRDR) of parC, gyrA, parE, and/or gyrB; *Streptococcus pneumoniae* bacteria comprising a mutation in ParC at S79-F or Y, D83-N, R95-C, or K137-N; *Streptococcus pneumoniae* bacteria comprising a mutation in gyrA at S83-A, C, F, or Y; E87-K; or S116-G; *Streptococcus pneumoniae* bacteria comprising a mutation in parE at D435-N or I460-V; *Streptococcus pneumoniae* bacteria comprising a mutation in gyrB at D435-N or E474-K; *Streptococcus pneumoniae* bacteria comprising at least four mutations in a QRDR or parC, gyrA, parE, and gyrB; and *Streptococcus pneumoniae* bacteria comprising a mutation in a quinolone resistance-determining region (QRDR) of parc, gyrA, parE, and/or gyrB.

Also provided is a method for modulating the activity of a topoisomerase comprising a mutation in a quinolone resistance-determining region (QRDR) of parC, gyrA or parE or gyrB.

It is preferred in the methods of the invention that said mutation in ParC is at S79-F or Y, D83-N, R95-C, or K137-N; said mutation in gyrA is at S83-A, C, F, or Y; E87-K; or S116-G; said mutation in parE is at D435-N or I460-V; or said mutation in gyrB is at D435-N or E474-K.

An object of the invention is a method for modulating metabolism of quinolone-resistant pneumococcal pathogenic bacteria comprising the step of contacting quinolone-resistant pneumococcal pathogenic bacteria with an antibacterially effective amount of a composition comprising a quinolone, particularly a gemifloxacin compound, or an antibacterially effective derivative thereof.

A further object of the invention is a method wherein said quinolone-resistant pneumococcal pathogenic bacteria is selected from the group consisting of: a pneumococcal strain comprising a mutation in the quinolone resistance-determining region (QRDR) of parC and/or gyrA; a pneumococcal strain comprising a mutation in parC said mutation comprising S79-F and/or Y, D83-G and/or N, N91-D, R95-C, and/or K137-N; a pneumococcal strain comprising a mutation in gyrA said mutation comprising S81-A, C, F, or Y; E85-K; and/or S114-G; a pneumococcal strain comprising a mutation in parE said mutation comprising D43 5-N and/or I460-V; a pneumococcal strain comprising a mutation in gyrB said mutation comprising D435-N and/or E474-K; a pneumococcal strain comprising a mutation in comprising three or four mutations in a QRDRs of parC, gyrA,parE, and/or gyrB; a pneumococcal strain comprising a mutation in comprising three or four mutations in a QRDRs of parC, gyrA,parE, and/or gyrB, any of which are resistant to ciprofloxacin, levofloxacin, or sparfloxacin; and a pneumococcal strain comprising a mutation in comprising three or four mutations in a QRDRs of parC, gyrA, parE, and/or gyrB, any of which also comprising an efflux mechanism of quinolone resistance.

Also provided by the invention is a method of treating or preventing a bacterial infection by quinolone-resistant pneumococcal pathogenic bacteria comprising the step of administering an antibacterially effective amount of a composition comprising a quinolone, particularly a gemifloxacin compound to a mammal suspected of having or being at risk of having an infection with quinolone-resistant pneumococcal pathogenic bacteria.

Further preferred methods are provided by the invention wherein said bacteria is selected from the group consisting of: a pneumococcal strain comprising a mutation in the quinolone resistance-determining region (QRDR) of parC and/or gyrA; a pneumococcal strain comprising a mutation in parC said mutation comprising S79-F and/or Y, D83-G and/or N, N91-D, R95-C, and/or K137-N; a pneumococcal strain comprising a mutation in gyrA said mutation comprising S81-A, C, F, and/or Y; E85-K; and/or S114-G; a pneumococcal strain comprising a mutation in parE said mutation comprising D435-N and/or I460-V; a pneumococcal strain comprising a mutation in gyrB said mutation comprising D435-N and/or E474-K; a pneumococcal strain comprising a mutation in comprising three or four mutations in a QRDRs of parC, gyrA, parE, and/or gyrB; a pneumococcal strain comprising a mutation in comprising three or four mutations in a QRDRs of parC, gyrA, parE, and/or gyrB, any of which are resistant to ciprofloxacin, levofloxacin, or sparfloxacin; and a pneumococcal strain comprising a mutation in comprising three or four mutations in a QRDRs of parC, gyrA, parE, and/or gyrB, any of which also comprising an efflux mechanism of quinolone resistance.

II. Haemophilus Pathogens

An object of the invention is a method for modulating metabolism of a rare *Haemophilus influenzae* strain comprising the step of contacting a rare *Haemophilus influenzae* strain with an antibacterially effective amount of a composition comprising a quinolone, particularly a gemifloxacin compound, or an antibacterially effective derivative thereof.

A further object of the invention is a method wherein said rare pathogenic *H. influenzae* strain is selected from the group consisting of: bacteria comprising a mutation set forth in Table 11 or 12; a *Haemophilus influenzae* strain set forth in Table 11 or 12; bacteria of the genus Haemophilus comprising a mutation set forth in Table 11 or 12; and bacteria of the species *Haemophilus influenzae* comprising a mutation set forth in Table 11 or 12.

Also provided by the invention is a method of treating or preventing a bacterial infection by a rare pathogenic *H. influenzae* strain comprising the step of administering an antibacterially effective amount of a composition comprising a quinolone, particularly a gemifloxacin compound to a mammal suspected of having or being at risk of having an infection with a rare pathogenic *H. influenzae* strain.

A preferred method is provided wherein said modulating metabolism is inhibiting growth of said bacteria or killing said bacteria.

A further preferred method is provided wherein said contacting said bacteria comprises the further step of introducing said composition into a mammal, particularly a human.

Further preferred methods are provided by the invention wherein said bacteria is selected from the group consisting of: bacteria comprising a mutation set forth in Table 11 or 12; a *Haemophilus influenzae* strain set forth in Table 11 or 12; bacteria of the genus Haemophilus comprising a mutation set forth in Table 11 or 12; and bacteria of the species *Haemophilus influenzae* comprising a mutation set forth in Table 11 or 12.

Various changes and modifications within the spirit and scope of the disclosed invention will become readily apparent to those skilled in the art from reading the following descriptions and from reading the other parts of the present disclosure.

DESCRIPTION OF THE INVENTION

I. Pneumococcal Pathogens

The present invention provides, among other things, methods for using a composition comprising a quinolone, particularly a gemifloxacin compound against a number of pathogenic bacteria including, for example, strains of *Streptococcus pneumoniae* and *Haemophilus influenzae*.

The present invention firther provides methods for using a composition comprising a quinolone, particularly a gemifloxacin compound against a quinolone-resistant pneumococcal strain, particularly a strain comprising a mutation in the quinolone resistance-determining region (QRDR) of parC and/or gyrA; a pneumococcal strain comprising a mutation in parC said mutation comprising S79-F and/or Y, D83-G and/or N, N91-D, R95-C, and/or K137-N; a pneumococcal strain comprising a mutation in gyrA said mutation comprising S81-A, C, F, and/or Y; E85-K; and/or S114-G; a pneumococcal strain comprising a mutation in parE said mutation comprising D435-N and/or I460-V; a pneumococcal strain comprising a mutation in grB said mutation comprising D435-N and/or E474-K; a pneumococcal strain comprising a mutation in comprising three or four mutations in a QRDRs of parC, gyrA, parE, and/or gyrB; a pneumococcal strain comprising a mutation in comprising three or four mutations in a QRDRs of parC, gyrA,parE, and/or gyrB, any of which are resistant to ciprofloxacin, levofloxacin, or sparfloxacin; and a pneumococcal strain comprising a mutation in comprising three or four mutations in a QRDRs of parC, gerA, parE, and/or gyrB, any of which also comprising an efflux mechanism of quinolone resistance.

As used herein "gemifloxacin compound(s)" means a compound having antibacterial activity described in patent application PCT/KR98/00051 published as WO 98/42705, or patent application EP 688772.

Previous studies have shown gemifloxacin to be 32 to 64 fold more active than ciprofloxacin, ofloxacin, sparfloxacin and trovafloxacin against methicillin-susceptible and -resistant *Staphylococcus aureus,* methicillin-resistant *Staphylococcus epideridis* and *S. pneumoniae.* Gemifloxacin was also highly active against most members of the family Enterobacteriaceae, with activity was more potent than those of sparfloxacin and ofloxacin and comparable to that of ciprofloxacin. Gemifloxacin was the most active agent against Gram-positive species resistant to other quinolones and glycopeptides. Gemifloxacin has limited activity against anaerobes (Cormican, et al., *Antimicrob. Agents Chemother.* 41:204–211, 1997; Hohl, et al., *Clin. Microbiol. Infect.* 4:280–284, 1998; Oh, et al., *Antimicrob. Agents Chemother.* 40:1564–1568, 1996).

This invention was based, in part, on analyses evaluating the comparative activity of gemifloxacin against various pneumococcal pathogens. In these analyses, gemifloxacin gave the lowest quinolone MICs against all pneumococcal strains tested followed by trovafloxacin, grepafloxacin, sparfloxacin, levofloxacin and ciprofloxacin. MICs were similar to those described previously (Cormican, et al., *Antimicrob. Agents Chemother.* 41:204–211, 1997; Hohl, et al., *Clin. Microbiol. Infect.* 4:280–284, 1998; Oh, et al., *Antimicrob. Agents Chemother.* 40:1564–1568, 1996). Additionally, gemifloxacin gave significantly lower MICs against highly quinolone resistant pneumococci, irrespective of quinolone resistance mechanism. This was the case in double mutants with mutations in both parC and gyrA, strains which have previously been shown to be highly resistant to other quinolones, as well as for strains with an efflux mechanism (Brenwald, et al., *Antimicrob. Agents Chemother.* 42:2032–2035, 1998; and Pan et al., *Antimicrob. Agents Chemother.* 40:2321–2326, 1996). MICs of non-quinolone agents were similar to those described previously (M. R. Jacobs, *Clin. Infect. Dis.* 15:119–127, 1992; Jacobs, et al., *Rev. Med. Microbiol.* 6:77–93, 1995; Pankuch, et al., *J. Antimicrob. Chemother.* 35:883–888, 1995).

Gemifloxacin also showed good killing against the 12 strains tested, including the two quinolone resistant strains. At $\leq 0.5$ µg/ml, gemifloxacin was bactericidal against all 12 strains. Killing rates relative to MICs were similar to those of other quinolones, with significant killing occurring earlier than β-lactams and macrolides. Kill kinetics of quinolone and non-quinolone compounds in the analyses described herein were similar to those described previously (Pankuch, et al., *Antimicrob. Agents Chemother.* 38:2065–2072, 1994; Pankuch et al., *Antimicrob. Agents Chemother.* 40:1653–1656, 1996; and Visalli, et al., *Antimicrob. Agents Chemother.* 40:362–366, 1996). Gemifloxacin also gave, together with the other quinolones tested, significant PAEs against all 6 strains tested, including the one quinolone resistant strain. The higher ciprofloxacin PAE at both exposure concentrations is of no significance, because, with an MIC of 32 μg/ml, 5× and 10×MIC are not clinically achievable with this strain. PAE values for quinolones and macrolides were similar to those described previously (Fuursted, et al., *Antimicrob. Agents Chemother.* 41:781–784, 1997; Licata, et al., *Antimicrob. Agents Chemother.* 41:950–955, 1997; Spangler, et al., *Antimicrob. Agents Chemother.* 41:2173–2176, 1997; and Spangler, et al., *Antimicrob. Agents Chemother.* 42:1253–1255, 1998). It is generally accepted that quinolones have similar PAEs against pneumococci.

In summary, gemifloxacin was the most potent quinolone tested by MIC and time-kill against both quinolone susceptible and resistant pneumococci and, similar to other quinolones, gave PAEs against quinolone susceptible strains. The incidence of quinolone resistant pneumococci is currently very low. However, this situation may change with the introduction of broad-spectrum quinolones into clinical practice, and in particular in the pediatric population, leading to selection of quinolone resistant strains (Davies, et al., *Antimicrob. Agents Chemother.* 43:1177–1182, 1999). Gemifloxacin is a promising new antipneumococcal agent against pneumococci, irrespective of their susceptibility to quinolones and other agents. Clinical studies will be necessary in order to validate this hypothesis.

Results of agar dilution MIC testing of the 207 strains with ciprofloxacin MICs ≦4.0 μg/ml are presented in Table 1. $MIC_{50/90}$ values (μg/ml) were as follows: gemifloxacin, 0.03/0.06; ciprofloxacin, 1.0/4.0; levofloxacin, 1.0/2.0; sparfloxacin, 0.5/0.5; grepafloxacin, 0.125/0.5; trovafloxacin, 0.125/0.25; amoxicillin, 0.016/0.06 (penicillin susceptible), 0.125/1.0 (penicillin intermediate), 2.0/4.0 (penicillin resistant); cefuroxime, 0.03/0.25 (penicillin susceptible), 0.5/2.0 (penicillin intermediate), 8.0/16.0 (penicillin resistant); azithromycin, 0.125/0.5 (penicillin susceptible), 0.125/>128.0 (penicillin intermediate), 4.0/>128.0 (penicillin resistant); clarithromycin, 0.03/0.06 (penicillin susceptible), 0.03/32.0 (penicillin intermediate), 2.0/>128.0 (penicillin resistant). Against 28 strains with ciprofloxacin MICs ≧8 μg/ml, gemifloxacin had the lowest MICs (0.03–1.0 μg/ml, $MIC_{90}$ 0.5 μg/ml), compared with MICs ranging between 0.25 to >32.0 μg/ml)($MIC_{90}$s 4.0–>32.0 μg/ml) for the other quinolones, with trovafloxacin, grepafloxacin, sparfloxacin and levofloxacin, in ascending order, giving the next lowest MICs (Table 2). Mechanisms of quinolone resistance are presented in Tables 3 and 4. As can be seen, quinolone resistance was associated with mutations in the quinolone resistance-determining region (QRDR) of parC, gyrA, parE, and/or gyrB. Mutations in ParC were at S79-F or Y, D83-N, R95-C, or K137-N. Mutations in gyrA were at S83-A, C, F, or Y; E87-K; or S116-G. Twenty one strains had a mutation in parE at D435-N or I460-V. Only two strains had a mutation in gyrB at D435-N or E474-K. Twenty strains had a total of three or four mutations in the QRDRs or parC, gyrA, parE, and gyrB (Table 3). Amongst these 20 strains all were resistant to ciprofloxacin (MICs >8 μg/ml), levofloxacin (MICs >4 μg/ml), and sparfloxacin (MICs >1 μg/ml); 19 were resistant to grepafloxacin (MICs >1 μg/ml); and 10 were resistant to trovafloxacin (MICs >2 μg/ml), yet gemifloxacin MICs were <0.5 μg/ml in 18 of the strains (Table 2).

In the presence of reserpine 23 strains had lower ciprofloxacin MICs (2–16×); 13 strains had lower gemifloxacin MICs (2–4×); 7 strains had lower levofloxacin MICs (2–4×); 3 strains bad lower grepafloxacin MICs (2×); and one strain had lower sparfloxacin MICs (2×), suggesting that an efflux mechanism contributed to the raised MICs in some cases (Table 4).

Microbroth dilution MIC results of the 12 strains tested by time-kill are presented in Table 5. Microdilution MICs were all within one dilution of agar MICs. For the two quinolone resistant strains (both penicillin susceptible), gemifloxacin microbroth MICs were 0.5 and 0.25 μg/ml, respectively. Time-kill results (Table 6) showed that levofloxacin at the MIC, gemifloxacin and sparfloxacin at 2×MIC and ciprofloxacin, grepafloxacin and trovafloxacin at 4×MIC, were bactericidal after 24 h. Various degrees of 90% and 99% killing by all quinolones was detected after 3 h. Gemifloxacin and trovafloxacin were both bactericidal at the microbroth MIC for the two quinolone resistant pneumococcal strains. Gemifloxacin was uniformly bactericidal after 24 h at ≦0.5 μg/ml. Amoxicillin, at 2×MIC and cefuroxime at 4×MIC, were bactericidal after 24 h, with some degree of killing at earlier time periods. By contrast, macrolides gave slower killing against the 7 susceptible strains tested, with 99.9% killing of all strains at 2–4×MIC after 24 hours.

For the five quinolone susceptible strains tested for PAE, MICs were similar to those obtained by microdilution, with gemifloxacin having MICs of 0.25 μg/ml against the quinolone resistant strain (MICs of other quinolones 4–32 μg/ml). PAEs (h)(10×MIC) for the 5 quinolone susceptible strains ranged between 0.4–1.6 for gemifloxacin; 0.5–1.5 h for ciprofloxacin (except for the quinolone resistant strain which gave a ciprofloxacin PAE of 6.3); 0.9–2.3 (levofloxacin); 0.3–2.0 (sparfloxacin); 0.3–2.6 (grepafloxacin); 1.3–3.0 (trovafloxacin). At 5×MIC, PAEs (h) for the quinolone resistant strain were 0.9 (gemifloxacin); 3.7 (ciprofloxacin); 1.3 (levofloxacin); 1.5 (sparfloxacin); 1.5 (grepafloxacin); 1.3 (trovafloxacin). PAEs for non-quinolone compounds (10×MIC) ranged between 0.3–5.8 (amoxicillin); 0.8–2.9 (cefuroxime); 1.3–3.0 (azithromycin); 1.8–4.5 (clarithromycin).

TABLE 1

Agar dilution MICs (μg/ml) of 207 quinolone susceptible strains[a]

| Drug | MIC range | $MIC_{50}$ | $MIC_{90}$ |
|---|---|---|---|
| Penicillin | | | |
| Penicillin S | ≦0.008–0.06 | 0.016 | 0.03 |
| Penicillin I | 0.125–1.0 | 0.25 | 1.0 |
| Penicillin R | 2.0–16.0 | 4.0 | 4.0 |
| Gemifloxacin | | | |
| Penicillin S | ≦0.008–0.125 | 0.03 | 0.03 |
| Penicillin I | ≦0.008–0.25 | 0.03 | 0.06 |
| Penicillin R | 0.004–0.125 | 0.03 | 0.06 |
| Ciprofloxacin | | | |
| Penicillin S | 0.25–4.0 | 1.0 | 2.0 |
| Penicillin I | 0.25–4.0 | 1.0 | 2.0 |
| Penicillin R | 0.5–4.0 | 1.0 | 4.0 |
| Levofloxacin | | | |
| Penicillin S | 0.125–4.0 | 1.0 | 2.0 |
| Penicillin I | 0.5–4.0 | 1.0 | 2.0 |
| Penicillin R | 1.0–2.0 | 1.0 | 2.0 |
| Sparfloxacin | | | |
| Penicillin S | ≦0.03–1.0 | 0.5 | 1.0 |
| Penicillin I | 0.06–2.0 | 0.5 | 0.5 |
| Penicillin R | 0.06–1.0 | 0.5 | 0.5 |

TABLE 1-continued

Agar dilution MICs (μg/ml) of 207 quinolone susceptible strains[a]

| Drug | MIC range | MIC$_{50}$ | MIC$_{90}$ |
|---|---|---|---|
| Grepafloxacin | | | |
| Penicillin S | ≦0.03–1.0 | 0.125 | 0.5 |
| Penicillin I | ≦0.03–0.5 | 0.125 | 0.5 |
| Penicillin R | ≦0.03–0.5 | 0.25 | 0.5 |
| Trovafloxacin | | | |
| Penicillin S | 0.03–0.5 | 0.125 | 0.25 |
| Penicillin I | 0.016–1.0 | 0.125 | 0.25 |
| Penicillin R | 0.03–0.25 | 0.125 | 0.25 |
| Amoxicillin | | | |
| Penicillin S | ≦0.008–0.25 | 0.016 | 0.06 |
| Penicillin I | 0.016–4.0 | 0.125 | 1.0 |
| Penicillin R | 0.5–8.0 | 2.0 | 4.0 |
| Cefuroxime | | | |
| Penicillin S | ≦0.008–2.0 | 0.03 | 0.25 |
| Penicillin I | 0.125–8.0 | 0.5 | 2.0 |
| Penicillin R | 0.5–32.0 | 8.0 | 16.0 |
| Azithromycin | | | |
| Penicillin S | ≦0.008–>128.0 | 0.125 | 0.5 |
| Penicillin I | ≦0.008–>128.0 | 0.125 | >128.0 |
| Penicillin R | 0.03–>128.0 | 4.0 | >128.0 |
| Clarithromycin | | | |
| Penicillin S | ≦0.008–>128.0 | 0.03 | 0.06 |
| Penicillin I | ≦0.008–>128.0 | 0.03 | 32.0 |
| Penicillin R | 0.008–>128.0 | 2.0 | >128.0 |

[a]Ciprofloxacin MICs ≦4.0 μg/ml.

TABLE 2

Quinolone agar dilution MICs (μg/ml) of 28 ciprofloxacin resistant strains[a]

| Quinolone | MIC range | MIC$_{50}$ | MIC$_{90}$ |
|---|---|---|---|
| Gemifloxacin | 0.3–1.0 | 0.25 | 0.5 |
| Ciprofloxacin | 8.0–>32.0 | 16.0 | >32.0 |
| Levofloxacin | 4.0–>32.0 | 16.0 | >32.0 |
| Sparfloxacin | 0.25–>32.0 | 8.0 | 16.0 |
| Grepafloxacin | 0.5–16.0 | 4.0 | 8.0 |
| Trovafloxacin | 0.25–8.0 | 1.0 | 4.0 |

[a]Ciprofloxacin MICs ≧8.0 μg/ml.

TABLE 3

Correlation of quinolone MIC (μg/ml) and mutation in quinolone resistant strains.

| Strain | Gemifloxacin[a] | Ciprofloxacin[a] | Levofloxacin[a] | Sparfloxacin[a] | Grepafloxacin[a] | Trovafloxacin[a] | ParC | ParE | GyrA | GryB |
|---|---|---|---|---|---|---|---|---|---|---|
| 1 | 0.03 | 16 | 8 | 4 | 4 | 2 | S79-F | I460-V | S83-F | None |
| 2 | 0.06 | 8 | 4 | 0.5 | 0.5 | 0.25 | S79-Y | I460-V | None | None |
| 3 | 0.06 | 8 | 4 | 1 | 0.5 | 0.25 | D83-N | I460-V | S83-F | None |
| 4 | 0.06 | 8 | 4 | 1 | 1 | 0.25 | S79-F | I460-V | S83-F | None |
| 5 | 0.125 | 8 | 8 | 1 | 1 | 0.25 | R95-C | D435-N | S83-F | None |
| 6 | 0.125 | 8 | 8 | 8 | 2 | 2 | S79-Y | I460-V | E87-K | None |
| 7 | 0.125 | 8 | 8 | 1 | 1 | 0.5 | None | I460-V | None | None |
| 8 | 0.125 | 8 | 8 | 1 | 1 | 0.5 | S79-Y | None | None | None |
| 9 | 0.125 | 8 | 8 | 2 | 1 | 1 | S79-Y | None | None | None |
| 10 | 0.125 | 8 | 8 | 4 | 2 | 1 | S79-F | I460-V | S83-C | None |
| 11 | 0.125 | 8 | 8 | 4 | 4 | 1 | S79-F | I460-V | S83-F | None |
| 12 | 0.125 | >32 | 16 | 1 | 4 | 1 | S79-F | I460-V | None | D435-N |
| 13 | 0.25 | 16 | 8 | 8 | 2 | 1 | S79-F | I460-V | None | EA74-K |
| 14 | 0.25 | 16 | 16 | 8 | 4 | 1 | S79-F | I460-V | S83-F | None |
| 15 | 0.25 | 16 | 16 | 8 | 4 | 1 | 79-F | I460-V | S83-F | None |
| 16 | 0.25 | 16 | 16 | 8 | 4 | 2 | S79-F | I460-V | S83-F | None |
| 17 | 0.25 | 16 | 16 | 8 | 4 | 2 | D83-N | None | S83-F | None |
| 18 | 0.25 | 16 | 16 | 8 | 4 | 2 | S79-F | I460-V | S83-F | None |
| 19 | 0.25 | 16 | 16 | 8 | 4 | 2 | S79-F | I460-V | S83-F | None |
| 20 | 0.25 | 32 | 16 | 8 | 4 | 2 | S79-F | I460-V | E87-K | None |
| 21 | 0.25 | 32 | 16 | 8 | 4 | 1 | S79-F | I460-V | S83-F | None |
| 22 | 0.25 | 32 | 16 | 8 | 4 | 2 | S79-F | I460-V | S83-Y | None |
| 23 | 0.25 | 32 | 16 | 8 | 8 | 2 | S79-Y | None | S83-A | None |
| 24 | 0.5 | 32 | 32 | 16 | 8 | 4 | S79-F | I460-V | S83-F | None |
| 25 | 0.5 | 32 | 32 | 16 | 8 | 4 | None | S83-F | None | |

TABLE 3-continued

Correlation of quinolone MIC (μg/ml) and mutation in quinolone resistant strains.

| Strain | Gemifloxacin[a] | Ciprofloxacin[a] | Levofloxacin[a] | Sparfloxacin[a] | Grepafloxacin[a] | Trovafloxacin[a] | ParC | ParE | GyrA | GryB |
|---|---|---|---|---|---|---|---|---|---|---|
| 26 | 0.5 | >32 | >32 | >32 | 8 | 4 | S79-F | None | S83-Y | None |
| 27 | 1 | >32 | >32 | >32 | 16 | 8 | S79-Y | I460-V | S83-F | None |
| 28 | 1 | >32 | >32 | >32 | 16 | 8 | None | S83-F | None S116-G | |

[a]MIC(μg/ml).

TABLE 4

Efflux mechanisms in quinolone resistant pneumococci

| Strain | Gemifloxacin | Ciprofloxacin | Levofloxacin | Sparfloxacin | Grepafloxacin | Trovafloxacin |
|---|---|---|---|---|---|---|
| 1 | 2 X[a] | 2 X | — | — | — | — |
| 2 | — | 8 x | — | — | — | — |
| 3 | — | — | — | — | — | — |
| 4 | — | — | — | — | — | — |
| 5 | 2 X | 4 X | — | 2 X | 2 X | — |
| 6 | — | 2 X | — | — | — | — |
| 7 | 2 X | 4 X | 2 X | — | — | — |
| 8 | 2 X | 2 X | — | — | — | — |
| 9 | 4 X | 8 X | — | — | — | — |
| 10 | — | 2 X | — | — | — | — |
| 11 | 2 X | 16 X | 4 X | — | — | — |
| 12 | 2 X | 4 X | 2 X | — | 2 X | — |
| 13 | — | 2 X | — | — | — | — |
| 14 | — | — | — | — | — | — |
| 15 | — | — | — | — | — | — |
| 16 | 2 X | 4 X | — | — | — | — |
| 17 | 2 X | 4 X | — | — | — | — |
| 18 | — | 2 X | — | — | — | — |
| 19 | — | 2 X | — | — | — | — |
| 20 | — | 2 X | — | — | — | — |
| 21 | — | 2 X | — | — | — | — |
| 22 | — | 2 X | — | — | — | — |
| 23 | 2 X | 8 X | 2 X | — | — | — |
| 24 | — | 2 x | — | — | — | — |
| 25 | 2 x | 4 x | 2 x | — | — | — |
| 26 | 2 x | 4 x | 2 x | — | — | — |
| 27 | — | — | — | — | — | — |
| 28 | 4 x | 8 x | 4 x | — | 2 X | — |

TABLE 5

Microdilution MICs of 12 strains tested by time-kill

| Drug | 1 (S)[a] | 2 (S) | 3 (S)[b] | 4 (S)[b] | 5 (I) | 6 (I) | 7 (I) | 8 (I) | 9 (R) | 10 (I) | 11 (R) | 12 (R) |
|---|---|---|---|---|---|---|---|---|---|---|---|---|
| Penicillin G | 0.06 | 0.03 | 0.016 | 0.016 | 0.25 | 0.25 | 1 | 0.5 | 4 | 2 | 4 | 4 |
| Gemifloxacin | 0.016 | 0.016 | 0.5 | 0.25 | 0.03 | 0.016 | 0.016 | 0.016 | 0.03 | 0.016 | 0.016 | 0.03 |
| Ciprofloxacin | 1 | 0.5 | 32 | 32 | 2 | 1 | 4 | 0.5 | 1 | 1 | 2 | 1 |
| Levofloxacin | 2 | 1 | 32 | 32 | 1 | 2 | 1 | 1 | 2 | 2 | 1 | 2 |
| Sparfloxacin | 0.125 | 0.25 | 32 | 16 | 0.5 | 0.25 | 0.25 | 0.25 | 0.5 | 0.25 | 0.25 | 0.5 |
| Grepafloxacin | 0.06 | 0.06 | 16 | 8 | 0.125 | 0.125 | 0.125 | 0.125 | 0.25 | 0.125 | 0.125 | 0.25 |
| Trovafloxacin | 0.06 | 0.06 | 8 | 4 | 0.06 | 0.06 | 0.06 | 0.125 | 0.125 | 0.06 | 0.06 | 0.125 |
| Amoxicillin | 0.016 | 0.016 | 0.008 | 0.008 | 0.03 | 0.125 | 0.125 | 0.06 | 1 | 1 | 2 | 2 |
| Cefuroxime | 0.5 | 0.25 | 0.016 | 0.016 | 0.5 | 0.5 | 0.5 | 0.25 | 2 | 0.5 | 2 | 2 |
| Azithromycin | 0.008 | 0.06 | >64 | 0.125 | >64 | 0.03 | 0.125 | 0.125 | >64 | >64 | 0.125 | >64 |
| Clarithromycin | 0.008 | 0.03 | >64 | 0.03 | 32 | 0.008 | 0.016 | 0.03 | >64 | >64 | 0.03 | >64 |

[a]S = penicillin susceptible;
I = penicillin intermediate;
R = penicillin resistant.
[b]Quinolone-resistant.

TABLE 6

Time-kill results of 12 pneumococcal strains

| Drug | 3h -1[a] | 3h -2[a] | 3h -3[a] | 6h -1 | 6h -2 | 6h -3 | 12h -1 | 12h -2 | 12h -3 | 24h -1 | 24h -2 | 24h -3 |
|---|---|---|---|---|---|---|---|---|---|---|---|---|
| Gemifloxacin | | | | | | | | | | | | |
| 8 × MIC | 10[b] | 2 | 0 | 12 | 8 | 2 | 12 | 12 | 9 | 12 | 12 | 12 |
| 4 × MIC | 9 | 1 | 0 | 12 | 8 | 0 | 12 | 12 | 8 | 12 | 12 | 12 |
| 2 × MIC | 6 | 0 | 0 | 12 | 7 | 0 | 12 | 11 | 8 | 12 | 12 | 12 |
| MIC | 4 | 1 | 0 | 11 | 2 | 0 | 12 | 8 | 3 | 12 | 10 | 8 |
| 0.5 × MIC | 1 | 0 | 0 | 4 | 0 | 0 | 3 | 0 | 0 | 2 | 2 | 0 |
| 0.25 × MIC | 0 | 0 | 0 | 0 | 0 | 0 | 0 | 0 | 0 | 0 | 0 | 0 |
| Ciprofloxacin | | | | | | | | | | | | |
| 8 × MIC | 10 | 8 | 2 | 12 | 11 | 6 | 12 | 12 | 10 | 12 | 12 | 12 |
| 4 × MIC | 9 | 6 | 1 | 12 | 10 | 5 | 12 | 12 | 10 | 12 | 12 | 12 |
| 2 × MIC | 9 | 4 | 0 | 12 | 8 | 2 | 12 | 12 | 6 | 12 | 12 | 11 |
| MIC | 4 | 0 | 0 | 8 | 3 | 0 | 10 | 9 | 3 | 11 | 10 | 6 |
| 0.5 × MIC | 0 | 0 | 0 | 1 | 1 | 0 | 2 | 1 | 0 | 2 | 1 | 0 |
| 0.25 × MIC | 0 | 0 | 0 | 0 | 0 | 0 | 0 | 0 | 0 | 0 | 0 | 0 |
| Levofloxacin | | | | | | | | | | | | |
| 8 × MIC | 11 | 3 | 0 | 12 | 9 | 4 | 12 | 12 | 10 | 12 | 12 | 12 |
| 4 × MIC | 10 | 4 | 0 | 12 | 9 | 1 | 12 | 12 | 8 | 12 | 12 | 12 |
| 2 × MIC | 10 | 2 | 0 | 12 | 9 | 1 | 12 | 12 | 9 | 12 | 12 | 12 |
| MIC | 9 | 1 | 0 | 12 | 6 | 0 | 12 | 11 | 7 | 12 | 12 | 12 |
| 0.5 × MIC | 4 | 1 | 0 | 8 | 1 | 0 | 7 | 3 | 0 | 8 | 7 | 5 |
| 0.25 × MIC | 0 | 0 | 0 | 0 | 0 | 0 | 0 | 0 | 0 | 0 | 0 | 0 |
| Sparfloxacin | | | | | | | | | | | | |
| 8 × MIC | 10 | 2 | 0 | 12 | 9 | 4 | 12 | 12 | 9 | 12 | 12 | 12 |
| 4 × MIC | 9 | 1 | 0 | 12 | 8 | 0 | 12 | 11 | 8 | 12 | 12 | 12 |
| 2 × MIC | 8 | 1 | 0 | 12 | 4 | 0 | 12 | 10 | 5 | 12 | 12 | 12 |
| MIC | 4 | 0 | 0 | 8 | 2 | 0 | 11 | 9 | 4 | 11 | 11 | 10 |
| 0.5 × MIC | 1 | 0 | 0 | 5 | 1 | 0 | 4 | 0 | 0 | 6 | 4 | 1 |
| 0.25 × MIC | 0 | 0 | 0 | 0 | 0 | 0 | 0 | 0 | 0 | 1 | 1 | 1 |
| Grepafloxacin | | | | | | | | | | | | |
| 8 × MIC | 8 | 2 | 1 | 12 | 5 | 2 | 12 | 11 | 7 | 12 | 12 | 12 |
| 4 × MIC | 6 | 0 | 0 | 12 | 4 | 0 | 12 | 10 | 5 | 12 | 12 | 12 |
| 2 × MIC | 3 | 0 | 0 | 9 | 1 | 0 | 10 | 8 | 1 | 11 | 10 | 9 |
| MIC | 1 | 0 | 0 | 4 | 1 | 0 | 7 | 3 | 0 | 8 | 5 | 3 |
| 0.5 × MIC | 0 | 0 | 0 | 0 | 0 | 0 | 1 | 0 | 0 | 1 | 1 | 0 |
| 0.25 × MIC | 0 | 0 | 0 | 0 | 0 | 0 | 0 | 0 | 0 | 0 | 0 | 0 |
| Trovafloxacin | | | | | | | | | | | | |
| 8 × MIC | 12 | 3 | 0 | 12 | 10 | 1 | 12 | 12 | 9 | 12 | 12 | 12 |
| 4 × MIC | 9 | 2 | 0 | 12 | 9 | 1 | 12 | 10 | 8 | 12 | 12 | 12 |
| 2 × MIC | 5 | 1 | 0 | 11 | 4 | 0 | 12 | 11 | 7 | 11 | 11 | 11 |
| MIC | 4 | 0 | 0 | 6 | 2 | 0 | 7 | 4 | 1 | 6 | 1 | 1 |
| 0.5 × MIC | 0 | 0 | 0 | 0 | 0 | 0 | 0 | 0 | 0 | 0 | 0 | 0 |
| 0.25 × MIC | 0 | 0 | 0 | 0 | 0 | 0 | 0 | 0 | 0 | 0 | 0 | 0 |
| Amoxicillin | | | | | | | | | | | | |
| 8 × MIC | 9 | 4 | 0 | 11 | 8 | 3 | 12 | 12 | 10 | 12 | 12 | 12 |
| 4 × MIC | 7 | 2 | 0 | 12 | 7 | 0 | 12 | 12 | 9 | 12 | 12 | 12 |
| 2 × MIC | 6 | 2 | 0 | 11 | 5 | 1 | 12 | 11 | 8 | 12 | 12 | 12 |
| MIC | 4 | 0 | 0 | 6 | 1 | 0 | 7 | 6 | 2 | 10 | 9 | 7 |
| 0.5 × MIC | 0 | 0 | 0 | 0 | 0 | 0 | 1 | 1 | 0 | 3 | 2 | 1 |
| 0.25 × MIC | 0 | 0 | 0 | 0 | 0 | 0 | 0 | 0 | 0 | 1 | 0 | 0 |
| Cefuroxime | | | | | | | | | | | | |
| 8 × MIC | 9 | 5 | 0 | 12 | 12 | 4 | 12 | 12 | 12 | 12 | 12 | 12 |
| 4 × MIC | 9 | 3 | 0 | 12 | 11 | 1 | 12 | 12 | 11 | 12 | 12 | 12 |
| 2 × MIC | 7 | 1 | 0 | 12 | 8 | 0 | 12 | 11 | 8 | 12 | 12 | 11 |
| MIC | 4 | 0 | 0 | 7 | 2 | 0 | 9 | 7 | 1 | 9 | 9 | 9 |
| 0.5 × MIC | 3 | 0 | 0 | 1 | 0 | 0 | 0 | 0 | 0 | 1 | 1 | 0 |
| 0.25 × MIC | 0 | 0 | 0 | 0 | 0 | 0 | 0 | 0 | 0 | 0 | 0 | 0 |
| Azithromycin[c] | | | | | | | | | | | | |
| 8 × MIC | 3 | 1 | 0 | 6 | 4 | 2 | 7 | 5 | 5 | 7 | 7 | 7 |
| 4 × MIC | 4 | 1 | 0 | 6 | 3 | 2 | 6 | 5 | 4 | 7 | 7 | 7 |
| 2 × MIC | 3 | 1 | 0 | 4 | 2 | 2 | 5 | 5 | 4 | 7 | 7 | 5 |
| MIC | 2 | 0 | 0 | 3 | 2 | 2 | 5 | 5 | 2 | 7 | 6 | 5 |
| 0.5 × MIC | 1 | 0 | 0 | 1 | 1 | 1 | 1 | 1 | 1 | 1 | 1 | 1 |
| 0.25 × MIC | 0 | 0 | 0 | 0 | 0 | 0 | 0 | 0 | 0 | 0 | 0 | 0 |
| Clarithromycin[c] | | | | | | | | | | | | |
| 8 × MIC | 4 | 2 | 0 | 7 | 2 | 2 | 5 | 5 | 5 | 7 | 7 | 7 |
| 4 × MIC | 3 | 2 | 0 | 7 | 2 | 2 | 5 | 5 | 5 | 7 | 7 | 7 |
| 2 × MIC | 3 | 2 | 0 | 5 | 2 | 2 | 5 | 5 | 4 | 7 | 7 | 7 |
| MIC | 3 | 1 | 0 | 5 | 0 | 1 | 5 | 5 | 2 | 7 | 7 | 5 |
| 0.5 × MIC | 1 | 0 | 0 | 3 | 0 | 0 | 1 | 1 | 1 | 4 | 3 | 1 |
| 0.25 × MIC | 0 | 0 | 0 | 0 | 0 | 0 | 0 | 0 | 0 | 0 | 0 | 0 |

[a]ΔLog10 cfu/ml lower than 0 h.
[b]No. strains tested.
[c]Only 7 strains with macrolide MICs ≤0.125 μg/ml were tested.

A further embodiment of the present invention is based, in part, on experiments wherein in vitro activity of gemifloxacin was compared with that of ciprofloxacin, levofloxacin, sparfloxacin, grepafloxacin and trovafloxacin against 28 pneumococci with ciprofloxacin MICs ≧8 μg/ml. Gemifloxacin MICs (μg/ml) ranged between 0.03–1.0 ($MIC_{50/90}$ 0.25/0.5), compared with ciprofloxacin 8→32 ($MIC_{50/90}$ 16/>32), levofloxacin 4→32 ($MIC_{50/90}$ 16/>32), sparfloxacin 0.25→32 ($MIC_{50/90}$ 8/16), grepafloxacin 0.5–16 ($MIC_{50/90}$ 4/8) and trovafloxacin 0.25–8 ($MIC_{50/90}$ 1.0/4.0). DNA sequence analysis showed that all but one strain had a mutation in the quinolone resistance-determining region (QRDR) of parC and/or gyrA. Mutations in parC were at S79-F or Y, D83-G or N, N91-D, R95-C, or K137-N. Mutations in gyrA were at S81-A, C, F, or Y; E85-K; or S114-G. Twenty-one strains had a mutation in parE at D435-N or I460-V. Only two strains had a mutation in gyrB at D435-N or E474-K. Twenty-one strains had a total of three or four mutations in the QRDRs of parC, gyrA, pare, and gyrB. Of these 21 strains, all were resistant to ciprofloxacin (MIC ≧8 μg/ml), levofloxacin (MIC ≧4 μg/ml), and sparfloxacin (MIC ≧1 μg/ml); 20 were resistant to grepafloxacin (MIC ≧1 μg/ml) and 11 were resistant to trovafloxacin (MIC ≧2 μ/ml), yet gemifloxacin MICs were ≦0.5 μg/ml in 19 of the strains. In the presence of reserpine, 23 strains had lower ciprofloxacin MICs (2–16x), 13 strains had lower gemifloxacin MICs (2–4x), 7 strains had lower levofloxacin MICs (2–4x); 3 strains had lower grepafloxacin MICs (2x) and one strain had lower sparfloxacin MICs (2x), indicating that an efflux mechanism contributed to the raised MICs in some cases. Results show that, irrespective of the mechanism of quinolone resistance, gemifloxacin showed the greatest in vitro activity against all pneumococcal strains tested. Against 28 strains with ciprofloxacin MICs ≧8 μg/ml, gemifloxacin had the lowest MICs (0.03–1.0 μg/ml, $MIC_{90}$ 0.5 μg/ml), compared with MICs ranging between 0.25 to >32.0 μg/ml ($MIC_{90}$ s4.0→32.0 μg/ml) for the other quinolones, with trovafloxacin, grepafloxacin, sparfloxacin and levofloxacin, in ascending order, giving the next lowest MICs (Table 7). Mechanisms of quinolone resistance are presented in Tables 8 and 9. As can be seen, quinolone resistance was associated with mutations in the quinolone resistance-determining region (QRDR) of parC, gyrA, parE and/or gyrB. Mutations in ParC were at S79-F or Y, D83-N, R95-C, or K137-N. Mutations in gyrA were at S83-A, C, F, or Y; E87-K; or S116-G. Twenty-one strains had a mutation in parE at D435-N or I460-V. Only two strains had a mutation in grB at D435-N or E474-K. Twenty-one strains had a total of three or four mutations in the QRDRs of parC, gyrA, pare and gyrB (Table 8). Amongst these 21 strains all were resistant to ciprofloxacin (MICs ≧8 µg/ml), levofloxacin (MICs ≧4 µg/ml), and sparfloxacin (MICs ≧1 µg/ml), 20 were resistant to grepafloxacin (MICs ≧1 µg/ml) and 11 were resistant to trovafloxacin (MICs ≧2 µg/ml), yet gemifloxacin MICs were ≦0.5 µg/ml in 19 of the strains (Table 8).

In the presence of reserpine 23 strains had lower ciprofloxacin MICs (2–16x), 13 strains had lower gemifloxacin MICs (2–4x), 7 strains bad lower levofloxacin MICs (2–4x); 3 strains had lower grepafloxacin MICs (2x); and one strain bad lower sparfloxacin MICs (2x), indicating that an efflux mechanism contributed to the raised MICs in some cases (Table 9). Previous studies have shown gemifloxacin to be 32 to 64 fold more active than ciprofloxacin, ofloxacin, sparfloxacin and trovafloxacin against methicillin-susceptible and -resistant *Staphylococcus aureus*, methicillin-resistant *Ataphylococcus epidennidis* and *S. pneumoniae* Gemifloxacin was also highly active against most members of the family Enterobacteriaceae, with activity which was more potent than those of sparfloxacin and ofloxacin and comparable to that of ciprofloxacin. Gemifloxacin was the most active agent against Gram positive species resistant to other quinolones and glycopeptides. Gemifloxacin has variable activity against anaerobes, and is very active against the Gram positive group (Cormican, et al., *Antimicrobiol. Agents Chemother.* 41 :204–211, 1997; Hohl, et al., *Clin. Microbiol. Infect.* 4:280–284, 1998; Oh, et al., *Antimicrob. Agents Chenother.* 40:1564–1568, 1996).

In our study, gemifloxacin gave significantly lower MICs against highly quinolone-resistant pneumococci, irrespective of quinolone resistance mechanism. This was the case in double mutants with mutations in both parC and gyrA, strains which have previously been shown to be highly resistant to other quinolones, as well as for strains with an efflux mechanism (Pan, et al., *Antimicrob. Agents Chemother.* 40:2321–2326, 1996 and Brenwald, et al., *Antimicrob. Agents Chemother.* 42:2032–2035, 1998).

In summary, gemifloxacin was the most potent quinolone tested against quinolone resistant pneumococci. The incidence of quinolone-resistant pneumococci is currently very low. However, this situation may change with the introduction of broad-spectrum quinolones into clinical practice, and in particular in the pediatric population, leading to selection of quinolone-resistant strains (Davies, et al., *Antimicrob. Agents Chemother.* 43:1177–1182, 1999). Results indicate that selective introduction of quinolones such as gemifloxacin into the pediatric environment is predicated upon toxicologic studies. Additionally, if the incidence of quinolone-resistant pneumococci increases, gemifloxacin will be a well-placed therapeutic option. Gemnifloxacin is a promising new antipneumococcal agent, irrespective of the strain's susceptibility to quinolones and other agents.

TABLE 7

Quinolone Agar Dilution MICs (µg/ml) of 28 Ciprofloxacin-Resistant Strains (MICs ≧8.0 µg/ml)

| Quinolone | MIC range | $MIC_{50}$ | $MIC_{90}$ |
| --- | --- | --- | --- |
| Gemifloxacin | 0.3–1.0 | 0.25 | 0.5 |
| Ciprofloxacin | 8.0–>32.0 | 16.0 | >32.0 |
| Levofloxacin | 4.0–>32.0 | 16.0 | >32.0 |
| Sparfloxacin | 0.25–>32.0 | 8.0 | 16.0 |
| Grepafloxacin | 0.5–16.0 | 4.0 | 8.0 |
| Trovafloxacin | 0.25–8.0 | 1.0 | 4.0 |

TABLE 8

Correlation of Quinolone MIC (µg/ml) and Mutation in Quinolone-Resistant Strains

| | MIC (µg/ml) | | | | | | Mutation | | | |
| --- | --- | --- | --- | --- | --- | --- | --- | --- | --- | --- |
| Strain | Gemifloxacin | Ciprofloxacin | Levofloxacin | Sparfloxacin | Grepafloxacin | Trovafloxacin | ParC | ParE | GyrA | GyrB |
| 1 | 0.03 | 16 | 8 | 4 | 4 | 2 | S79-F | I460-V | S81-F | None |
| 2 | 0.06 | 8 | 4 | 0.5 | 0.5 | 0.25 | S79-Y | I460-V | None | None |
| 3 | 0.06 | 8 | 4 | 1 | 0.5 | 0.25 | D83-N | I460-V | S81-F | None |
| 4 | 0.06 | 8 | 4 | 1 | 1 | 0.25 | S79-F | I460-V | S81-F | None |
| 5 | 0.125 | 8 | 8 | 1 | 1 | 0.25 | R95-C | D435-N | S81-F | None |
| 6 | 0.125 | 8 | 8 | 8 | 2 | 2 | S79-Y | I460-V | E85-K | None |
| 7 | 0.125 | 8 | 8 | 1 | 1 | 0.5 | None | I460-V | None | None |
| 8 | 0.125 | 8 | 8 | 1 | 1 | 0.5 | S79-Y | None | None | None |
| 9 | 0.125 | 8 | 8 | 2 | 1 | 1 | S79-Y | None | None | None |
| 10 | 0.125 | 8 | 8 | 4 | 2 | 1 | S79-F | I460-V | S81-C | None |
| 11 | 0.125 | 8 | 8 | 4 | 4 | 1 | S79-F | I460-V | S81-F | None |
| 12 | 0.125 | >32 | 16 | 1 | 4 | 1 | S79-F | I460-V | None | D435-N |
| 13 | 0.25 | 16 | 8 | 8 | 2 | 1 | S79-F | I460-V | None | EA74-K |
| 14 | 0.25 | 16 | 16 | 8 | 4 | 1 | S79-F | I460-V | S81-F | None |
| 15 | 0.25 | 16 | 16 | 8 | 4 | 1 | S79-F | I460-V | S81-F | None |
| 16 | 0.25 | 16 | 16 | 8 | 4 | 2 | S79-F | I460-V | S81-F | None |
| 17 | 0.25 | 16 | 16 | 8 | 4 | 2 | D83-N | None | S81-F | None |
| 18 | 0.25 | 16 | 16 | 8 | 4 | 2 | S79-F | I460-V | S81-F | None |
| 19 | 0.25 | 16 | 16 | 8 | 4 | 2 | S79-F | I460-V | S81-F | None |

TABLE 8-continued

Correlation of Quinolone MIC (μg/ml) and Mutation in Quinolone-Resistant Strains

| Strain | MIC (μg/ml) | | | | | | Mutation | | | |
|---|---|---|---|---|---|---|---|---|---|---|
| | Gemifloxacin | Ciprofloxacin | Levofloxacin | Sparfloxacin | Grepafloxacin | Trovafloxacin | ParC | ParE | GyrA | GyrB |
| 20 | 0.25 | 32 | 16 | 8 | 4 | 2 | S79-F | I460-V | E85-K | None |
| 21 | 0.25 | 32 | 16 | 8 | 4 | 1 | S79-F | I460-V | S81-F | None |
| 22 | 0.25 | 32 | 16 | 8 | 4 | 2 | S79-F | I460-V | S81-Y | None |
| 23 | 0.25 | 32 | 16 | 8 | 8 | 2 | S79-Y | None | S81-A | None |
| 24 | 0.5 | 32 | 32 | 16 | 8 | 4 | S79-F | I460-V | S81-F | None |
| 25 | 0.5 | 32 | 32 | 16 | 8 | 4 | D83-G N91-D | None | S81-F | None |
| 26 | 0.5 | >32 | >32 | >32 | 8 | 4 | S79-F | None | S81-Y | None |
| 27 | 1 | >32 | >32 | >32 | 16 | 8 | S79-Y | I460-V | S81-F | None |
| 28 | 1 | >32 | >32 | >32 | 16 | 8 | D83G N91-D | None | S81-F S114-G | None |

TABLE 9

Efflux Mechanisms in Quinolone-Resistant Pneumococci

| Strain | Gemifloxacin | Ciprofloxacin | Levofloxacin | Sparloxacin | Grepafloxacin | Trovafloxacin |
|---|---|---|---|---|---|---|
| 1 | 2 X[a] | 2 X | — | — | — | — |
| 2 | — | 8 x | — | — | — | — |
| 3 | — | — | — | — | — | — |
| 4 | — | — | — | — | — | — |
| 5 | 2 X | 4 X | — | 2 X | 2 X | — |
| 6 | — | 2 X | — | — | — | — |
| 7 | 2 X | 4 X | 2 X | — | — | — |
| 8 | 2 X | 2 X | — | — | — | — |
| 9 | 4 X | 8 X | — | — | — | — |
| 10 | — | 2 X | — | — | — | — |
| 11 | 2 X | 16 X | 4 X | — | — | — |
| 12 | 2 X | 4 X | 2 X | — | 2 X | — |
| 13 | — | 2 X | — | — | — | — |
| 14 | — | — | — | — | — | — |
| 15 | — | — | — | — | — | — |
| 16 | 2 X | 4 X | — | — | — | — |
| 17 | 2 X | 4 X | — | — | — | — |
| 18 | — | 2 X | — | — | — | — |
| 19 | — | 2 X | — | — | — | — |
| 20 | — | 2 X | — | — | — | — |
| 21 | — | 2 X | — | — | — | — |
| 22 | — | 2 X | — | — | — | — |
| 23 | 2 X | 8 X | 2 X | — | — | — |
| 24 | — | 2 x | — | — | — | — |
| 25 | 2 x | 4 x | 2 x | — | — | — |
| 26 | 2 x | 4 x | 2 x | — | — | — |
| 27 | — | — | — | — | — | — |
| 28 | 4 x | 8 x | 4 x | — | 2 X | — |

[a]Number of dilutions decrease after incubation with reserpine (see Materials and Methods). National Committee for Clinical Laboratory Standards. 1997. Methods for dilution antimicrobial susceptibility tests for bacteria that grow aerobically -- third edition; approved standard. NCCLS publication no. M7-A4. National Committee for Clinical Laboratory Standards, Villanova, PA.

II. Haemophilus Pathogens

Nine quinolone-resistant *H. influenzae* strains yielded MIC$_{50}$s of 0.25 μg/ml for gemifloxacin (highest MIC 1.0 μg/ml) compared to 1.0 μg/ml (highest MIC 4.0–8.0 μg/ml) for the other quinolones tested (Table 10). Mechanisms of quinolone resistance in the *H. influenzae* strains are presented in Table 11. All nine strains had mutations at Ser 84 in GyrA with Ser 84 to Leu, Phe, or Tyr observed. Additional mutations in GyrA at Asp 88 to Asn or Tyr, and Ala 117 to Glu were also observed in some strains. Most strains also had at least one mutation in ParC (at Asp 83, Ser 84, Glu 88, Ser 133, or Asn 138) and ParE (at Gly 405, Asp 420, Ser 458, or Ser 474). Strain 4 had an in-frame insertion in parE that led to an insertion of a Ser residue in between Ser 458 and Thr 459. Only one strain had a mutation in GyrB (at Gln 468). The most resistant strain (strain 9) had double mutations in GyrA, ParC and ParE.

Previous studies have shown gemifloxacin to be 32–64 fold more active than ciprofloxacin, ofloxacin, sparfloxacin and trovafloxacin against methicillin-susceptible and -resistant *S. aureus*, methicillin-resistant *Staphylococcus epideridis* and *S. pneumoniae*. Gemifloxacin was also highly active against most members of the family Enterobacteriaceae, with activity more potent than those of sparfloxacin and ofloxacin and comparable to that of ciprofloxacin. Gemifloxacin was the most active agent against Gram positive species resistant to other quinolones and glycopeptides. Gemifloxacin has variable activity against anaerobes and is very active against the Gram positive group (Cormican, et al., *Antimicrob. Agents Chemother.* 41:204–211, 1997; Hohl, et al., *Clin. Microbiol. Infect.* 4:280–284, 1998; and Oh, et al., *Antimicrob. Agents Chemother.* 40:1564–1568, 1996. In the studies set forth herein, only gemifloxacin gave MICs $\leq 1.0\,\mu g/ml$ against the rare strains of *H. influenzae* with raised quinolone MICs. Previous studies (Bootsma, et al., *J. Antimicrob. Chemother.* 39:292–293, 1997; Georgiou, et al., *Antimicrob. Agents Chemother.* 40:1741–1744, 1996; and Vila, et al., *Antimicrob. Agents Chemother.* 43:161–162, 1999) have shown that the primary target of quinolones in *H. influenzae* is GyrA; low-level resistance is associated with a mutation in GyrA (Ser 84 or Asp 88) and high-level resistance with an additional mutation in ParC (Asp 83, Ser 84 or Glu 88). Sequencing results from this study were in agreement with the above previous reports, as all nine strains had at least one mutation in GyrA and the most resistant strains (ciprofloxacin MICs $\geq 1.0\,\mu g/ml$) had an additional mutation in ParC. Mutations were found in GyrA (Ala 117) and ParC (Ser 133, Asn 138) that have not been previously reported. Provided herein is a novel examination of mutations in GyrB and ParE in *H. influenzae*: most strains had mutations in ParE, but only one strain in GyrB. Of particular interest was insertion of a serine between serine 458 and threonine 459 of ParE in one strain. It, therefore, appears that ParE is more important in quinolone resistance in *H. influenzae* than GyrB.

Results of this study indicate excellent activity of gernifloxacin against quinolone-resistant i H. influenzae (including those with multiple mutations) by MIC. Because of the wide spectrum of activity of gemifloxacin against other respiratory pathogens, such as pneumococci (including quinolone-resistant strains), Legionella, mycoplasmas and chlamydia, this compound represents an attractive alternative to other quinolone and non-quinolone agents for empiric treatment of community-acquired respiratory tract infections.

TABLE 10

Quinolone MICs ($\mu g/ml$) for 9 Quinolone-Resistant *Haemophilus influenzae* strains

| Antimicrobial | Range | $MIC_{50}$ |
|---|---|---|
| Gemifloxacin | 0.03–1.0 | 0.25 |
| Ciprofloxacin | 0.25–8.0 | 1.0 |
| Levofloxacin | 0.25–4.0 | 1.0 |
| Sparfloxacin | 0.25–8.0 | 1.0 |
| Grepafloxacin | 0.25–4.0 | 1.0 |
| Trovafloxacin | 0.25–8.0 | 1.0 |

TABLE 11

Mechanisms of Resistance in Quinolone-Resistant *Haemophilus influenzae* strains

| Strain | Gemi | Cipro | Levo | Spar | Grepa | Trova | Mutation | | | |
|---|---|---|---|---|---|---|---|---|---|---|
| 1 | 0.03 | 0.5 | 0.5 | 0.25 | 0.25 | 1 | S133-A N138-S | None | S84-L | None |
| 2 | 0.125 | 0.25 | 0.25 | 0.25 | 0.5 | 0.25 | NONE | S458-L | S84-F | None |
| 3 | 0.125 | 1 | 1 | 0.5 | 0.5 | 1 | S84-I | None | S84-L | None |
| 4 | 0.25 | 1 | 0.5 | 0.25 | 2 | 0.5 | D83-N | S458-S-T459 | S84-F D88-N | Q468-R |
| 5 | 0.25 | 1 | 1 | 1 | 1 | 1 | E88-K | G405-S | S84-Y | None |
| 6 | 0.5 | 2 | 2 | | 1 | 4 | S84-R | D420-N | S84-L A117-E | None |
| 7 | 0.5 | 2 | 2 | 1 | 1 | 4 | S84-R | D420-N | S84-L A117-E | None |
| 8 | 0.5 | 2 | 2 | 1 | 1 | 4 | S84-R | D420-N | S84-L A117-E | None |
| 9 | 1 | 8 | 4 | 8 | 4 | 8 | S84-R N138-S | S458-A S474-N | S84-F D88-Y | None |

TABLE 12

| | MICs ($\mu g/ml$) | | | | | | Mutation | | | |
|---|---|---|---|---|---|---|---|---|---|---|
| Strain | Gem | Cip | Lev | Spa | Gre | Tro | GyrA | ParC | GyrB | ParE |
| 1 | 0.03 | 0.5 | 0.5 | 0.25 | 0.25 | 1 | S84-L | S133-A N138-S | None | None |
| 2 | 0.125 | 0.25 | 0.25 | 0.25 | 0.5 | 0.25 | S84-F | None | None | S458-L |
| 3 | 0.125 | 1 | 1 | 0.5 | 0.5 | 1 | S84-L | S84-I | None | None |
| 4 | 0.25 | 1 | 0.5 | 0.25 | 2 | 0.5 | S84-F D88-N | D83-N | None | T459-S |
| 5 | 0.25 | 1 | 1 | 1 | 1 | 1 | S84-Y | E88-K | Q468-R | G405-S |
| 6 | 0.5 | 2 | 2 | 1 | 1 | 4 | S84-L A117-E | S84-R | None | D420-N |
| 7 | 0.5 | 2 | 2 | 1 | 1 | 4 | S84-L A117-E | S84-R | None | D420-N |

TABLE 12-continued

| | MICs (μg/ml) | | | | | | Mutation | | | |
|---|---|---|---|---|---|---|---|---|---|---|
| Strain | Gem | Cip | Lev | Spa | Gre | Tro | GyrA | ParC | GyrB | ParE |
| 8 | 0.5 | 2 | 2 | 1 | 1 | 4 | S84-L A117-E | S840-R | None | D420-N |
| 9 | 1 | 8 | 4 | 8 | 4 | 8 | S84-F D88-Y | S84-R N138-S | None | S458-A S474-N |

All strains had mutations at position 84 in gyrA, and the most R strain had double mutations in gyrA, parC and parE. Strains with mutations at position 84 in parC and gyrA plus mutations in parE were tro R. Gem had the lowest MICs against all strains irrespective of their mutation mechanism.

The invention provides a method for modulating metabolism of a rare pathogenic *H. influenzae* strain. Skilled artisans can readily choose a rare pathogenic *Haemophilus. influenzae* strain or patients infected with or suspected to be infected with these organisms to practice the methods of the invention. Alternatively, the bacteria useful in the methods of the invention may be those described herein.

The invention provides a method for modulating metabolism of pneumococcal and Haemophilus pathogenic bacteria. Skilled artisans can readily choose pneumococcal and Haemophilus pathogenic bacteria or patients infected with or suspected to be infected with these organisms to practice the methods of the invention. Alternatively, the bacteria useful in the methods of the invention may be those described herein.

The contacting step in any of the methods of the invention may be performed in many ways that will be readily apparent to the skilled artisan. However, it is preferred that the contacting step is a provision of a composition comprising a gemifloxacin compound to a human patient in need of such composition or directly to bacteria in culture medium or buffer.

For example, when contacting a human patient or contacting said bacteria in a human patient or in vitro, the compositions comprising a quinolone, particularly a gemifloxacin compound, preferably pharmaceutical compositions may be administered in any effective, convenient manner including, for instance, administration by topical, oral, anal, vaginal, intravenous, intraperitoneal, intramuscular, subcutaneous, intranasal or intradermal routes among others.

It is also preferred that these compositions be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a compound of the invention, a quinolone, preferably a gemifloxacin compound, and a pharmaceutically acceptable carrier or excipient. Such carriers may include, but are not limited to, saline, buffered saline, dextrose, water, glycerol, ethanol and combinations thereof. The formulation should suit the mode of administration.

Quinolone compounds, particularly gemifloxacin compounds and compositions of the methods of the invention may be employed alone or in conjunction with other compounds, such as bacterial efflux pump inhibitor compounds or antibiotic compounds, particularly non-quinolone antibiotic compounds, e.g., beta-actam antibiotic compounds.

In therapy or as a prophylactic, the active agent of a method of the invention is preferably administered to an individual as an injectable composition, for example as a sterile aqueous dispersion, preferably an isotonic one.

Alternatively, the gemifloxacin compounds or compositions in the methods of the invention may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the antibacterially effective amount is a daily dosage level of the active agent from 0.001 mg/kg to 10 mg/kg, typically around 0.1 mg/kg to 1 mg/kg, preferably about 1 mg/kg. A physician, in any event, will determine an actual dosage that is most suitable for an individual and will vary with the age, weight and response of the particular individual. The above dosages are exemplary of the average case. There can, of course, be individual instances where higher or lower dosage ranges are merited, and such are within the scope of this invention. It is preferred that the dosage is selected to modulate metabolism of a bacteria in such a way as to inhibit or stop growth of said bacteria or by killing said bacteria. The skilled artisan may identify this amount as provided herein as well as using other methods known in the art, e.g. by the application MIC tests.

A further embodiment of the invention provides for the contacting step of the methods to further comprise contacting an in-dwelling device in a patient. In-dwelling devices include, but are not limited to, surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, and continuous ambulatory peritoneal dialysis (CAPD) catheters.

A quinolone, particularly a gemifloxacin compound or composition of the invention may be administered by injection to achieve a systemic effect against relevant bacteria, preferably a pneumococcal or Haemophilus pathogenic bacteria, shortly before insertion of an in-dwelling device. Treatment may be continued after surgery during the in-body time of the device. In addition, the composition could also be used to broaden perioperative cover for any surgical technique to prevent bacterial wound infections caused by or related to pneumococcal or Haemophilus pathogenic bacteria.

In addition to the therapy described above, a gemifloxacin compound or composition used in the methods of this invention may be used generally as a wound treatment agent to prevent adhesion of bacteria to matrix proteins, particularly pneumococcal or Haemophilus pathogenic bacteria, exposed in wound tissue and for prophylactic use in dental treatment as an alternative to, or in conjunction with, antibiotic prophylaxis.

Alternatively, a quinolone, particularly a gemifloxacin compound or composition of the invention may be used to bathe an indwelling device immediately before insertion. The active agent will preferably be present at a concentration of 1 µg/ml to 10 mg/ml for bathing of wounds or indwelling devices.

Also provided by the invention is a method of treating or preventing a bacterial infection by pneumococcal or Haemophilus pathogenic bacteria comprising the step of administering an antibacterially effective amount of a composition comprising a quinolone, particularly a gemifloxacin compound to a mammal, preferably a human, suspected of having or being at risk of having an infection with pneumococcal or Haemophilus pathogenic bacteria.

A preferred object of the invention provides a method wherein said pneumococcal pathogenic bacteria is selected from the group consisting of: bacteria comprising a mutation in a quinolone resistance-determining region (QRDR) of parc, gyrA, parE, and/or gyrB; bacteria comprising a mutation in ParC at S79-F or Y, D83-N, R95-C, or K137-N; bacteria comprising a mutation in gyrA at S83-A, C, F, or Y; E87-K; or S116-G; bacteria comprising a mutation in parE at D435-N or I460-V; bacteria comprising a mutation in gyrB at D435-N or E474-K; bacteria comprising at least four mutations in a QRDR or parC, gyrA, parE, and gyrB; bacteria comprising a mutation in a quinolone resistance-determining region (QRDR) of parC, gyrA, parE, and/or gyrB; bacteria that are ciprofloxacin-resistant, levofloxacin-resistant, sparfloxacin-resistant, grepafloxacin-resistant, or trovafloxacin-resistant, or a combination thereof, that comprise a mutation in ParC at S79-F or Y, D83-N, R95-C, or K137-N; bacteria that are ciprofloxacin-resistant, levofloxacin-resistant, sparfloxacin-resistant, grepafloxacin-resistant, or trovafloxacin-resistant, or a combination thereof, that comprise a mutation in gyrA at S83-A, C, F, or Y; E87-K; or S116-G; bacteria that are ciprofloxacin-resistant, levofloxacin-resistant, sparfloxacin-resistant, grepafloxacin-resistant, or trovafloxacin-resistant, or a combination thereof, that comprise a mutation in parE at D435-N or I460-V; bacteria that are ciprofloxacin-resistant, levofloxacin-resistant, sparfloxacin-resistant, grepafloxacin-resistant, or trovafloxacin-resistant, or a combination thereof, that comprise a mutation in gyrB at D435-N or E474-K; bacteria that are ciprofloxacin-resistant, levofloxacin-resistant, sparfloxacin-resistant, grepafloxacin-resistant, or trovafloxacin-resistant, or a combination thereof, that comprise at least four mutations in a QRDR or parC, gyrA, parE, and gyrB; bacteria that are ciprofloxacin-resistant, levofloxacin-resistant, sparfloxacin-resistant, grepafloxacin-resistant, or trovafloxacin-resistant, or a combination thereof, that comprise a mutation in a quinolone resistance-determining region (QRDR) of parC, gyrA, parE, and/or gyrB; *Streptococcus pneumoniae* bacteria comprising a mutation in ParC at 879-F or Y, D83-N, R95-C, or K137-N; *Streptococcus pneumoniae* bacteria comprising a mutation in gyrA at S83-A, C, F, or Y; E87-K; or S116-G; *Streptococcus pneumoniae* bacteria comprising a mutation in parE at D435-N or I460-V; *Streptococcus pneumoniae* bacteria comprising a mutation in gyrB at D435-N or E474-K; *Streptococcus pneumoniae* bacteria comprising at least four mutations in a QRDR or parC, gyrA, parE, and gyrB; and *Streptococcus pneumoniae* bacteria comprising a mutation in a quinolone resistance-determining region (QRDR) of parC, gyrA, parE, and/or gyrB.

A preferred object of the invention provides a method wherein said quinolone-resistant pneumococcal pathogenic bacteria is selected from the group consisting of: a pneumococcal strain comprising a mutation in the quinolone resitance-determining region (QRDR) of parC and/or gyrA; a pneumococcal strain comprising a mutation in parC said mutation comprising S79-F and/or Y, D83-G and/or N, N91-D, R95-C, and/or K137-N; a pneumococcal strain comprising a mutation in gyrA said mutation comprising S81-A, C, F, and/or Y; E85-K; and/or S114-G; a pneumococcal strain comprising a mutation in parE said mutation comprising D435-N and/or I460-V; a pneumococcal strain comprising a mutation in gyrB said mutation comprising D435-N and/or E474-K; a pneumococcal strain comprising a mutation in comprising three or four mutations in a QRDRs of parC, gyrA, parE, and/or gyrB; a pneumococcal strain comprising a mutation in comprising three or four mutations in a QRDRs of parC, gyrA, parE, and/or gyrB, any of which are resistant to ciprofloxacin, levofloxacin, or sparfloxacin; and a pneumococcal strain comprising a mutation in comprising three or four mutations in a QRDRs of parC, gyrA, parE, and/or gyrB, any of which also comprising an efflux mechanism of quinolone resistance.

A further preferred object of the invention provides a method wherein said rare pathogenic *H. influenzae* strain is selected from the group consisting of: bacteria comprising a mutation set forth in Table 11 or 12; a *Haemophilus influenzae* strain set forth in Table 11 or 12; bacteria of the genus Haemophilhs comprising a mutation set forth in Table 11 or 12; and bacteria of the species *Haemophilus influenzae* comprising a mutation set forth in Table 11 or 12.

Other pneumococcal and Haemophilus pathogenic bacteria may also be included in the methods. The skilled artisan may identify these organisms as provided herein as well as using other methods known in the art, e.g. MIC tests.

Preferred embodiments of the invention include, among other things, methods wherein said composition comprises gemifloxacin, or a pharmaceutically acceptable derivative thereof.

EXAMPLES

The present invention is further described by the following examples. The examples are provided solely to illustrate the invention by reference to specific embodiments. This exemplification's, while illustrating certain specific aspects of the invention, do not portray the limitations or circumscribe the scope of the disclosed invention.

All examples were carried out using standard techniques, which are well known and routine to those of skill in the art, except where otherwise described in detail.

All parts or amounts set out in the following examples are by weight, unless otherwise specified.

Example 1

Bacteria

For agar dilution MICs, quinolone susceptible pneumococci comprised 64 penicillin susceptible (MICs ≦0.06 µg/ml), 68 penicillin intermediate (MICs 0.125–1.0 µg/ml) and 75 penicillin resistant (MIC 2.0–16.0 µg/ml) strains (all quinolone susceptible, with ciprofloxacin MICs ≦4.0 µg/ml). All susceptible, and some intermediate and resistant strains, were recent U.S. isolates. The remainder of intermediate and resistant strains were isolated in South Africa, Spain, France, Central and Eastern Europe, and Korea.

Additionally, 28 strains with ciprofloxacin MICs ≧8 μg/ml some from a collection of organisms were tested by agar dilution. Additionally these strains were tested for mutations in parC, gyrA, parE, and gyrB (Pan, et al., *Antimicrob. Agents Chemother.* 40:2321–2326, 1996) and for efflux mechanism (Brenwald, et al., *Antimicrob. Agents Chemother.* 42:2032–2035, 1998). For time-kill studies, 4 penicillin susceptible, 4 intermediate and 4 resistant strains (2 quinolone resistant) were tested, while for PAE studies 5 quinolone susceptible and 1 resistant strains were studied.

Example 2
Antimicrobials and MIC Testing

Agar dilution methodology was performed on 234 strains as described previously (M. R. Jacobs, *Clin. Infect. Dis.* 15:119–127, 1992; Jacobs, et al., *Rev. Med. Microbiol.* 6:77–93, 1995), using Mueller-Histon agar (BBL Microbiology Systems, Cockeysville, Md.) supplemented with 5% sheep blood. Broth MICs for 12 strains tested by time-kill and 6 tested by PAE were performed according to NCCLS recommendations (Methods for Dilution Antimicrobial Susceptibility Tests for Bacteria that Grow Aerobically, 3rd Edition, NCCLS, Villanova, Pa.) using cation-adjusted Mueller-Hinton broth with 5% lysed defibrinated horse blood. Standard quality control strains, including *Streptococcus pneumoniae* ATCC 49619, were included in each run of agar and broth dilution MICs.

Example 3
Time-kill Testing

For time-kill studies, glass tubes containing 5 ml cation-adjusted Mueller-Hinton broth (Difco) +5% lysed horse blood with doubling antibiotic concentrations were inoculated with $5 \times 10^5$ to $5 \times 10^6$ cfu/ml and incubated at 35° C. in a shaking water bath. Antibiotic concentrations were chosen to comprise 3 doubling dilutions above and 3 dilutions below the agar dilution MIC. Growth controls with inoculum but no antibiotic were included with each experiment (Pankuch, et al., *Antimicrob. Agents Chemother.* 38:2065–2072, 1994; Pankuch, et al., *Antimicrob. Agents Chemother* 40:1653–1656, 1996).

Lysed horse blood was prepared as described previously. The bacterial inoculum was prepared by diluting a 16 h broth (medium as above) culture in the same medium. Dilutions required to obtain the correct inoculum ($5 \times 10^5$–$5 \times 10^6$ cfu/ml) were determined by prior viability studies using each strain (Pankuch, et al., *Antimicrob. Agents Chemother.* 38:2065–2072, 1994; Pankuch, et al., *Antimicrob. Agents Chemother.* 40:1653–1656, 1996).

To inoculate each tube of serially diluted antibiotic, 50 ìof diluted inoculum was delivered by pipette beneath the surface of the broth. Tubes were then vortexed and plated for viability counts within 10 min (approximately 0.2 h). The original inoculum was determined by using the untreated growth control. Only tubes containing an initial inoculum within the range of $5 \times 10^5$ to $5 \times 10^6$ cfu/ml were acceptable (Pankuch, et al., *Antimicrob. Agents Chemother.* 38:2065–2072, 1994; Pankuch, et al., *Antimicrob. Agents Chemother.* 40:1653–1656, 1996).

Viability counts of antibiotic-containing suspensions were performed by plating ten-fold dilutions of 0.1 ml aliquots from each tube in sterile Mueller-Hinton broth onto trypticase soy agar 5% sheep blood agar plates (BBL). Recovery plates were incubated for up to 72 h. Colony counts were performed on plates yielding 30–300 colonies. The lower limit of sensitivity of colony counts was 300 cfu/ml (Pankuch, et al., *Antimicrob. Agents Chemother.* 38:2065–2072, 1994; Pankuch, et al., *Antimicrob. Agents Chemother.* 40:1653–1656, 1996).

Time-kill assays were analysed by determining the number of strains which yielded a $\log_{10}$ cfu/ml of −1, −2 and −3 at 0, 3, 6, 12 and 24 h, compared to counts at time 0 h. Antimicrobials were considered bactericidal at the lowest concentration that reduced the original inoculum by ≧3 $\log_{10}$ cfu/ml (99.9%) at each of the time periods, and bacteriostatic if the inoculum was reduced by 0–3 $\log_{10}$ cfu/ml. With the sensitivity threshold and inocula used in these studies, no problems were encountered in delineating 99.9% killing, when present. The problem of bacterial carryover was addressed as described previously. For macrolide time-kill testing, only strains with MICs ≦4.0 μg/ml were tested (Pankuch, et al., *Antimicrob. Agents Chemother.* 38:2065–2072, 1994; Pankuch, et al., *Antimicrob. Agents Chemother.* 40:1653–1656, 1996).

Example 4
Post-antibiotic Effect Testing

The post-antibiotic effect (PAE) (Craig, et al., V. Lorian (ed.) *Antibiotics in Laboratory Medicine,* Williams and Wilkins, Baltimore, pages 296–329, 1996) was determined by the viable plate count method, using Mueller-Hinton broth (MHB) supplemented with 5% lysed horse blood when testing pneumococci. The PAE was induced by exposure to 10×MIC for 1 h (Craig, et al., V. Lorian (ed.) *Antibiotics in Laboratory Medicine,* Williams and Wilkins, Baltimore, pages 296–329, 1996; Spangler, et al., *Antimicrob. Agents Chemother.* 41:2173–2176, 1997; Spangler, et al., *Antimicrob. Agents Chemother.* 42:1253–1255, 1998.) Additionally, the one quinolone resistant strain was exposed at quinolone concentrations 5×MIC. Tubes containing 5 ml broth with antibiotic were inoculated with approximately $5 \times 10^6$ cfu/ml. Growth controls with inoculum but no antibiotic were included with each experiment. Tubes were placed in a shaking water bath at 35° C. for 1 h. At the end of the exposure period, cultures were diluted 1:1000 to remove antibiotic. A control containing bacteria pre-exposed to antibiotic at a concentration of 0.01×MIC was also prepared (Spangler, et al., *Antimicrob. Agents Chemother.* 41:2173–2176, 1997; Spangler, et al., *Antimicrob. Agents Chemother.* 42:1253–1255, 1998).

Viability counts were determined before exposure and immediately after dilution (0 h), and then every 2 h until tube turbidity reached a #1 McFarland standard. Inocula were prepared by suspending growth from an overnight blood agar plate in broth. The broth was incubated at 35° C. for 2–4 h in a shaking water bath until turbidity matched a #1 McFarland standard, and checked for viability by plate counts (Spangler, et al., *Antimicrob. Agents Chemother.* 41:2173–2176, 1997; Spangler, et al., *Antimicrob. Agents Chemother.* 42:1253–1255, 1998).

The PAE was defined as PAE=T−C; T=time required for viability counts of an antibiotic-exposed culture to increase by 1 $\log_{10}$ above counts immediately after dilution; C=corresponding time for growth control. For each experiment, viability counts ($\log_{10}$ cfu/ml) were plotted against time, and results expressed as the mean of two separate assays ±SD (Craig, et al., V. Lorian (ed.), *Antibiotics in Laboratory Medicine,* Williams and Wilkins, Baltimore, pages 296–329, 1996).

Example 5
PCR of Quinolone Resistance Determinants and DNA Sequence Analysis

Polymerase chain reaction method (PCR) was used to amplify parC, parE, gyrA, and gyrB using primers and cycling conditions described by Pan and Fisher (Pan, et al., *Antimicrob. Agents Chemother.* 40:2321–2326, 1996). Template DNA for PCR was prepared using Prep-A-Gene kit (Bio-Rad, Hercules, Calif.) as recommended by the manufacturer. After amplification PCR products were purified from excess primers and nucleotides using QIAquick PCR Purification kit as recommended by the manufacturer (Qiagen, Valencia, Calif.) and sequenced directly using Applied Biosystems Model 373A DNA sequencer. Strains with mutations widely described in the literature (e.g. Ser79-Tyr or Phe in ParC and Ser83-Tyr or Phe in GyrA) were sequenced once in the forward direction. Strains with no mutations in any of the above mentioned genes or with a previously undescribed mutation were sequenced twice in the forward direction and once in the reverse direction on products of independent PCR reactions (Davies, et al., *Antimicrob. Agents Chemother.* 43:1177–1182, 1999).

Example 6

Determination of Efflux Mechanism

MICs were determined in the presence and absence of 10 µg/ml of reserpine (Sigma Chemicals, St. Louis, Mo.) as known in the art. Strains with at least a twofold lower ciprofloxacin MIC in the presence of reserpine were then tested against the other quinolones in the presence of reserpine. Results were repeated three times Brenwald et al., *Antimicrob. Agents Chemother.* 42:2032–2035, 1998; Davies, et al., *Antimicrob. Agents Chemother.* 43:1177–1182, 1999).

Example 7

Bacterial Strains 28 strains with ciprofloxacin MICs ≧8 µg/ml were tested by agar dilution. Additionally these strains were tested for mutations in parC, gyrA, parE, and gyrB (Pan, et al., *Antimicrob. Agents Chemother.* 40:2321–2326, 1996) and for efflux mechanism (Brenwald, et al., *Antimicrob. Agents Chemother.* 42:2032–2035,1998).

Example 8

Antimicrobials and MIC Testing

Gemifloxacin susceptibility powder was obtained from SmithKline Beecham Laboratories, Harlow, UK. Agar dilution methodology was performed on 28 strains as described previously (M. R. Jacobs, *Clin. Infect. Dis.* 15:119–127, 1992 and M. R. Jacobs, *Rev. Med. Microbiol.* 6:77–93, 1995), using Mueller-Hinton agar (BBL Microbiology Systems, Cockeysville, Md.) supplemented with 5% sheep blood. Standard quality control strains, including *Streptococcus pneumoniae* ATCC 49619, were included in each run of agar dilution MICs.

Example 9

PCR of Quinolone Resistance Determinants and DNA Sequence Analysis

PCR was used to amplify parC, parE, gyrA and gyrB using primers and cycling conditions described by Pan et al (Pan et al., *Antimicrob. Agents Chemother.* 40:2321–2326, 1996). Template DNA for PCR was prepared using Prep-A-Gene kit (Bio-Rad, Hercules, Calif., USA) as recommended by the manufacturer. After amplification PCR products were purified from excess primers and nucleotides using QIAquick PCR Purification kit as recommended by the manufacturer (Qiagen, Valencia, Calif., USA) and sequenced directly using Applied Biosystems Model 373A DNA sequencer.

Example 10

Determination of Efflux Mechanism

MICs were determined in the presence and absence of 10 µg/ml of reserpine (Sigma row Chemicals, St. Louis, Mo., USA) as described previously (Brenwald, et al., *Antimicrob. Agents Chemother.* 42:2032–2035, 1998 and Davies, et al., *Antimicrob. Agents Chemother.* 43:1177–1182, 1999). Strains with at least a twofold lower ciprofloxacin MIC in the presence of reserpine were then tested against the other quinolones in the presence of reserpine. Results were repeated three times previously (Brenwald, et al., *Antimicrob. Agents Chemother.* 42:2032–2035, 1998 and Davies, et al., *Antimicrob. Agents Chemother.* 43:117714–1182, 1999).

Example 11

Bacterial Strains and Antimicrobials

Gemifloxacin susceptibility powder was obtained from SmithKline Beecham Laboratories, Harlow, UK.

Example 12

MIC Determination

Inocula were prepared from chocolate agar plates incubated for a full 24 hours by the direct colony suspension method as follows: In a tube of Mueller-Hinton broth (Difco), an organism suspension was made to a density of a 0.5 McFarland standard ($1\times10^8$ CFU/ml). The latter inoculum was diluted in sterile saline such that final organisms suspensions in trays yielded colony counts of $3–8\times10^5$ CFU/ml. Frozen microdilution trays were obtained from MicroMedia Systems, Inc. (Cleveland, Ohio, USA). Each tray contained all antimicrobials prepared in freshly made HTM. Wells were inoculated with 100 µl suspensions and incubated in ambient air at 35° C. for 20–24 hours. The lowest drug concentration showing no growth was read as the MIC. Standard quality control strains, including *H. influenzae* ATCC 49766, *H. influenzae* ATCC 49247, *Staphylococcus aureus* ATCC 29213 and *Escherichia coli* ATCC 25922 were included with each run.

Example 13

PCR and DNA Sequencing of Quinolone-resistant Determining Region of parC, parE, gyrA, and gyrB Template DNA for PCR was prepared as follows: a colony from overnight growth was lysed by incubation for 1 hour at 37° C. in lysis buffer (6 mM Tris-HCL [pH 7.4], 1 M NaCl, 10 mM EDTA [pH 8.0], 0.2% deoxycholate, 0.5% sodium lauroyl sarcosine) to which lysozyme (Sigma, St. Louis, Mo., USA) at 0.5 mg/ml and lysostaphin (Sigma) at 0.05 mg/ml were added fresh. DNA was isolated from the lysed cells using a Prep-A-Gene kit (Bio-Rad, Hercules, Calif., USA) as recommended by the manufacturer. PCR was carried out in a final volume of 100 µl containing 10 mM Tris-HCl (pH 8.3), 50 mM KCl, 1.5 mM MgCl$_2$, 200 µM each dNTPS, 5 pmol of each primer, 5–10 ng DNA template, and 2.5 U Taq DNA polymerase (Fisher Biotech). Conditions for PCR were 30 cycles of 94° C. for 1 minute, annealing at 53° C. for 1 minute, and extension at 72° C. from 3 minutes. For parC a 370 bp region encoding residues 41 to 163 was amplified using primers HFPARCUP (5'-TGGTTTAAAACCCGTTCA-3', nucleotide positions 120 to 137) (SEQ. ID NO:1), and HFPARCDN (5'-AGCAGGTAAATAITGTGG-3', positions 473–490) (SEQ ID NO:2). For parE a 471 bp region encoding residues 335 to 491 was amplified using primers HFPAREUP (5'-GAACGCTTATCATCACGCCA-3', positions 1003 to 1022) (SEQ ID NO:3) and HFPAREDN (5'-AGCATCCGCGAGAATACAGA-3', positions 1454 to 1473) (SEQ ID NO:4). For gyrA a 375 bp region encoding residues 47 to 171 was amplified using primers BFGYRAUP (5'-CCGCCGCGTACTGTTCT-3', positions 138 to 154) (SEQ ID NO:5) and HFGYRADN (5'-CCATTTGCTAAAAGTGC-3', positions 496 to 512)(SEQ ID NO:6). For gyrB a 445 bp region encoding residues 367 to 513 was amplified using primers HFGYRBFOR (5'-GGAAAATCCTGCAGATGC-3', positions 1095 to 1113) (SEQ ID NO:7) and HFGYRBBAC (5'-AAGCAACGTACGGATGTG-3', positions 1522 to 1539) (SEQ ID NO:8). After amplification PCR products were purified from excess primers and nucleotides using a QIAquick PCR purification kit (Qiagen, Valencia, Calif., USA) and sequenced directly by using an Applied Biosystems model 373A DNA sequencer. All genes were sequenced twice in the forward and reverse directions on products of independent PCRs.

Each reference cited herein is hereby incorporated by reference in its entirety. Moreover, each patent application to which this application claims priority is hereby incorporated by reference in its entirety.

What is claimed is:

1. A method for modulating metabolism of pneumococcal pathogenic bacteria comprising the step of contacting pneumococcal pathogenic bacteria with an antibacterially effective amount of a composition comprising a gemifloxacin compound, or an antibacterially effective derivative thereof, wherein said pneumococcal pathogenic bacteria is selected from the group consisting of:

bacteria comprising a mutation in a quinolone resistance-determining region (QRDR) of parC, gyrA, parE, and/or gyrB;

bacteria comprising a mutation in parC at S79-F or Y, D83-N, R95-C, or K137-N;

bacteria comprising a mutation in gyrA at S83-A, C, F, or Y; E87-K; or S116-G;

bacteria comprising a mutation in parE at D435-N or I460-V;

bacteria comprising a mutation in gyrB at D435-N or E474-K;

bacteria comprising at least four mutations in a QRDR of parC, gyrA, parE, and gyrB;

bacteria that are ciprofloxacin-resistant, levofloxacin-resistant, sparfloxacin-resistant, grepafloxacin-resistant, or trovafloxacin-resistant, or a combination thereof, that comprise a mutation in parC at S79-F or Y, D83-N, R95-C, or K137-N;

bacteria that are ciprofloxacin-resistant, levofloxacin-resistant, sparfloxacin-resistant, grepafloxacin-resistant, or trovafloxacin-resistant, or a combination thereof, that comprise a mutation in gyrA at S83-A, C, F, or Y; E87-K; or S116-G;

bacteria that are ciprofloxacin-resistant, levofloxacin-resistant, sparfloxacin-resistant, grepafloxacin-resistant, or trovafloxacin-resistant, or a combination thereof, that comprise a mutation in parE at D435-N or I460-V;

bacteria that are ciprofloxacin-resistant, levofloxacin-resistant, sparfloxacin-resistant, grepafloxacin-resistant, or trovafloxacin-resistant, or a combination thereof, that comprise a mutation in gyrB at D435-N or E474-K;

bacteria that are ciprofloxacin-resistant, levofloxacin-resistant, sparfloxacin-resistant, grepafloxacin-resistant, or trovafloxacin-resistant, or a combination thereof, that comprise at least four mutations in a QRDR of parC, gyrA, parE, and gyrB;

bacteria that are ciprofloxacin-resistant, levofloxacin-resistant, sparfloxacin-resistant, grepafloxacin-resistant, or trovafloxacin-resistant, or a combination thereof, that comprise a mutation in a quinolone resistance-determining region (QRDR) of parC, gyrA, parE, and/or gyrB;

Streptococcus pneumoniae bacteria comprising a mutation in parC at S79-F or Y, D83-N, R95-C, or K137-N;

Streptococcus pneumoniae bacteria comprising a mutation in gyrA at S83-A, C, F, or Y; E87-K; or S116-G;

Streptococcus pneumoniae bacteria comprising a mutation in parE at D435-N or I460-V;

Streptococcus pneumoniae bacteria comprising a mutation in gyrB at D435-N or E474-K;

Streptococcus pneumoniae bacteria comprising at least four mutations in a QRDR of parC, gyrA, parE, and gyrB; and Streptococcus pneumoniae bacteria comprising a mutation in a quinolone resistance-determining region (QRDR) of parc, gyrA, parE, and/or gyrB.

2. The method of claim 1 wherein said modulating metabolism is inhibiting growth of said bacteria.

3. The method of claim 1 wherein said modulating metabolism is killing said bacteria.

4. The method of claim 1 wherein said contacting said bacteria comprises the further step of introducing said composition into a mammal.

5. The method of claim 4 wherein said mammal is a human.

6. A method of treating or preventing a bacterial infection by pneumococcal pathogenic bacteria comprising the step of administering an antibacterially effective amount of a composition comprising a gemifloxacin compound, or an antibacterially effective derivative thereof, to a mammal suspected of having or being at risk of having an infection with pneumococcal pathogenic bacteria, wherein said pneumococcal pathogenic bacteria is selected from the group consisting of:

bacteria comprising a mutation in a quinolone resistance-determining region (QRDR) of parC, gyrA, parE, and/or gyrB;

bacteria comprising a mutation in parC at S79-F or Y, D83-N, R95-C, or K137-N;

bacteria comprising a mutation in gyra at S83-A, C, F, or Y; E87-K; or S116-G;

bacteria comprising a mutation in parE at D435-N or I460-V;

bacteria comprising a mutation in gyrB at D435-N or E474-K;

bacteria comprising at least four mutations in a QRDR of parC, gyrA, parE, and gyrB;

bacteria that are ciprofloxacin-resistant, levofloxacin-resistant, sparfloxacin-resistant, grepafloxacin-resistant, or trovafloxacin-resistant, or a combination thereof, that comprise a mutation in parC at S79-F or Y, D83-N, R95-C, or K137-N;

bacteria that are ciprofloxacin-resistant, levofloxacin-resistant, sparfloxacin-resistant, grepafloxacin-resistant, or trovafloxacin-resistant, or a combination thereof, that comprise a mutation in gyrA at S83-A, C, F, or Y; E87-K; or S116-G;

bacteria that are ciprofloxacin-resistant, levofloxacin-resistant, sparfloxacin-resistant, grepafloxacin-resistant, or trovafloxacin-resistant, or a combination thereof, that comprise a mutation in parE at D435-N or I460-V;

bacteria that are ciprofloxacin-resistant, levofloxacin-resistant, sparfloxacin-resistant, grepafloxacin-resistant, or trovafloxacin-resistant, or a combination thereof, that comprise a mutation in gyrB at D435-N or E474-K;

bacteria that are ciprofloxacin-resistant, levofloxacin-resistant, sparfloxacin-resistant, grepafloxacin-resistant, or trovafloxacin-resistant, or a combination thereof, that comprise at least four mutations in a QRDR of parC, gyrA, parE, and gyrB;

bacteria that are ciprofloxacin-resistant, levofloxacin-resistant, sparfloxacin-resistant, grepafloxacin-resistant, or trovafloxacin-resistant, or a combination thereof, that comprise a mutation in a quinolone resistance-determining region (QRDR) of parC, gyrA, parE, and/or gyrB;

*Streptococcus pneumoniae* bacteria comprising a mutation in parC at S79-F or Y, D83-N, R95-C, or K137-N;

*Streptococcus pneumoniae* bacteria comprising a mutation in gyrA at S83-A, C, F, or Y; E87-K; or S116-G;

*Streptococcus pneumoniae* bacteria comprising a mutation in parE at D435-N or I460-V;

*Streptococcus pneumoniae* bacteria comprising a mutation in gyrB at D435-N or E474-K;

*Streptococcus pneumoniae* bacteria comprising at least four mutations in a QRDR of parC, gyrA, parE, and gyrB; and

*Streptococcus pneumoniae* bacteria comprising a mutation in a quinolone resistance-determining region (QRDR) of parC, gyrA, parE, and/or gyrB.

7. The method of claim 6 wherein said mammal is a human.

8. The method of claim 6 wherein said pneumococcal pathogenic bacteria is a *Streptococcus pneumoniae* bacteria comprising a mutation in parC at S79-F or Y, D83-N, R95-C, or K137-N.

9. The method of claim 6 wherein said pneumococcal pathogenic bacteria is a *Streptococcus pneumoniae* bacteria comprising a mutation in gyrA at S83-A, C, F, or Y; E87-K; or S116-G.

10. The method of claim 6 wherein said pneumococcal pathogenic bacteria is a *Streptococcus pneumoniae* bacteria comprising a mutation in parE at D435-N or I460-V.

11. The method of claim 6 wherein said pneumococcal pathogenic bacteria is a *Streptococcus pneumoniae* bacteria comprising a mutation in gyrB at D435-N or E474-K.

12. The method of claim 6 wherein said pneumococcal pathogenic bacteria is a *Streptococcus pneumoniae* bacteria comprising at least four mutations in a QRDR of parC, gyrA, parE, and gyrB.

13. The method of claim 6 wherein said pneumococcal pathogenic bacteria is a *Streptococcus pneumoniae* bacteria comprising a mutation in a quinolone resistance-determining region (QRDR) of parC, gyra, parE, and/or gyrB.

14. A method for modulating metabolism of quinolone-resistant pneumococcal pathogenic bacteria comprising the step of contacting quinolone-resistant pneumococcal pathogenic bacteria with an antibacterially effective amount of a composition comprising a gemifloxacin compound, or an antibacterially effective derivative thereof, wherein said quinolone-resistant pneumococcal pathogenic bacteria is selected from the group consisting of:

a pneumococcal strain comprising a mutation in the quinolone resistance-determining region (QRDR) of parC and/or gyrA;

a pneumococcal strain comprising a mutation in parC, said mutation comprising S79-F and/or Y, D83-G and/or N, N91-D, R95-C, and/or K137-N;

a pneumococcal strain comprising a mutation in gyrA, said mutation comprising S81-A, C, F, and/or Y; E85-K; and/or S114-G;

a pneumococcal strain comprising a mutation in parE, said mutation comprising D435-N and/or I460-V;

a pneumococcal strain comprising a mutation in gyrB, said mutation comprising D435-N and/or E474-K;

a pneumococcal strain comprising three or four mutations in a QRDRs of parC, gyrA, parE, and/or gyrB;

a pneumococcal strain comprising three or four mutations in a QRDRs of parC, gyrA, parE, and/or gyrB, any of which are resistant to ciprofloxacin, levofloxacin, or sparfloxacin; and a pneumococcal strain comprising three or four mutations in a QRDRs of parC, gyrA, parE, and/or gyrB, any of which also comprising an efflux mechanism of quinolone resistance.

15. The method of claim 14 wherein said modulating metabolism is inhibiting growth of said bacteria.

16. The method of claim 14 wherein said modulating metabolism is killing said bacteria.

17. The method of claim 14 wherein said contacting said bacteria comprises the further step of introducing said composition into a mammal.

18. The method of claim 17 wherein said mammal is a human.

19. The method of claim 14 wherein said quinolone-resistant pneumococcal pathogenic bacteria is a pneumococcal strain comprising a mutation in parC, said mutation comprising S79-F and/or Y, D83-G and/or N, N91-D, R95-C, and/or K137-N.

20. The method of claim 14 wherein said quinolone-resistant pneumococcal pathogenic bacteria is a pneumococcal strain comprising a mutation in gyrA, said mutation comprising S81-A, C, F, and/or Y; E85-K; and/or S114-G.

21. The method of claim 14 wherein said quinolone-resistant pneumococcal pathogenic bacteria is a pneumococcal strain comprising a mutation in parE, said mutation comprising D435-N and/or I460-V.

22. The method of claim 14 wherein said quinolone-resistant pneumococcal pathogenic bacteria is a pneumococcal strain comprising a mutation in gyrB, said mutation comprising D435-N and/or E474-K.

23. The method of claim 14 wherein said quinolone-resistant pneumococcal pathogenic bacteria is a pneumococcal strain comprising three or four mutations in a QRDRs of parC, gyrA, parE, and/or gyrB.

24. The method of claim 14 wherein said quinolone-resistant pneumococcal pathogenic bacteria is a pneumococcal strain comprising three or four mutations in a QRDRs of parC, gyrA, parE, and/or gyrB, any of which are resistant to ciprofloxacin, levofloxacin, or sparfloxacin.

25. The method of claim 14 wherein said quinolone-resistant pneumococcal pathogenic bacteria is a pneumococcal strain comprising three or four mutations in a QRDRs of parC, gyrA, parE, and/or gyrB, any of which also comprising an efflux mechanism of quinolone resistance.

26. A method of treating or preventing a bacterial infection by quinolone-resistant pneumococcal pathogenic bacteria comprising the step of administering an antibacterially effective amount of a composition comprising a gemifloxacin compound, or an antibacterially effective derivative thereof, to a mammal suspected of having or being at risk of having an infection with quinolone-resistant pneumococcal pathogenic bacteria, wherein said quinolone-resistant pneumococcal pathogenic bacteria is selected from the group consisting of:

a pneumococcal strain comprising a mutation in the quinolone resistance-determining region (QRDR) of parC and/or gyrA;

a pneumococcal strain comprising a mutation in parC, said mutation comprising S79-F and/or Y, D83-G and/or N, N91 -D, R95-C, and/or K137-N;

a pneumococcal strain comprising a mutation in gyrA, said mutation comprising S81-A, C, F, and/or Y; E85-K; and/or S114-G;

a pneumococcal strain comprising a mutation in parE, said mutation comprising D435-N and/or I460-V;

a pneumococcal strain comprising a mutation in gyrB, said mutation comprising D435-N and/or E474-K;

a pneumococcal strain comprising three or four mutations in a QRDRs of parC, gyrA, parE, and/or gyrB;

a pneumococcal strain comprising three or four mutations in a QRDRs of parC, gyrA, parE, and/or gyrB, any of which are resistant to ciprofloxacin, levofloxacin, or sparfloxacin; and a pneumococcal strain comprising three or four mutations in a QRDRs of parC, gyrA, parE, and/or gyrB, any of which also comprising an efflux mechanism of quinolone resistance.

27. The method of claim 14 wherein said mammal is a human.

28. The method of claim 26 wherein said quinolone-resistant pneumococcal pathogenic bacteria is a pneumococcal strain comprising a mutation in parC, said mutation comprising S79-F and/or Y, D83-G and/or N, N91-D, R95-C, and/or K137-N.

29. The method of claim 26 wherein said quinolone-resistant pneumococcal pathogenic bacteria is a pneumococcal strain comprising a mutation in gyrA, said mutation comprising S81-A, C, F, and/or Y; E85-K; and/or S114-G.

30. The method of claim 26 wherein said quinolone-resistant pneumococcal pathogenic bacteria is a pneumococcal strain comprising a mutation in parE, said mutation comprising D435-N and/or I460-V.

31. The method of claim 26 wherein said quinolone-resistant pneumococcal pathogenic bacteria is a pneumococcal strain comprising a mutation in gyrB, said mutation comprising D435-N and/or E474-K.

32. The method of claim 26 wherein said quinolone-resistant pneumococcal pathogenic bacteria is a pneumococcal strain comprising three or four mutations in a QRDRs of parC, gyrA, parE, and/or gyrB.

33. The method of claim 26 wherein said quinolone-resistant pneumococcal pathogenic bacteria is a pneumococcal strain comprising three or four mutations in a QRDRs of parC, gyrA, parE, and/or gyrB, any of which are resistant to ciprofloxacin, levofloxacin, or sparfloxacin.

34. The method of claim 26 wherein said quinolone-resistant pneumococcal pathogenic bacteria is a pneumococcal strain comprising three or four mutations in a QRDRs of parC, gyrA, parE, and/or gyrB, any of which also comprising an efflux mechanism of quinolone resistance.

* * * * *

UNITED STATES PATENT AND TRADEMARK OFFICE
CERTIFICATE OF CORRECTION

PATENT NO. : 6,803,376 B1
DATED : October 12, 2004
INVENTOR(S) : Peter C. Applbaum et al.

It is certified that error appears in the above-identified patent and that said Letters Patent is hereby corrected as shown below:

Column 34,
Line 40, "parc," should read -- *parC*, --.
Line 64, "gyra" should read -- *gyrA* --.

Column 35,
Line 32, "sparfioxacin-resistant," should read -- sparfloxacin-resistant, --.

Column 36,
Line 8, "gyra," should read -- *gyrA*, --.

Column 37,
Line 30, "N91 -D," should read -- N91-D, --.

Column 38,
Line 7, "claim 14" should read -- claim 26 --.

Signed and Sealed this

Seventh Day of June, 2005

JON W. DUDAS
*Director of the United States Patent and Trademark Office*

SEQUENCE LISTING

```
<160> NUMBER OF SEQ ID NOS: 8

<210> SEQ ID NO 1
<211> LENGTH: 18
<212> TYPE: DNA
<213> ORGANISM: Haemophilus influenzae

<400> SEQUENCE: 1
tggtttaaaa cccgttca                                                 18

<210> SEQ ID NO 2
<211> LENGTH: 18
<212> TYPE: DNA
<213> ORGANISM: Haemophilus influenzae

<400> SEQUENCE: 2
agcaggtaaa tattgtgg                                                 18

<210> SEQ ID NO 3
<211> LENGTH: 20
<212> TYPE: DNA
<213> ORGANISM: Haemophilus influenzae

<400> SEQUENCE: 3
gaacgcttat catcacgcca                                               20

<210> SEQ ID NO 4
<211> LENGTH: 20
<212> TYPE: DNA
<213> ORGANISM: Haemophilus influenzae

<400> SEQUENCE: 4
agcatccgcg agaatacaga                                               20

<210> SEQ ID NO 5
<211> LENGTH: 17
<212> TYPE: DNA
<213> ORGANISM: Haemophilus influenzae

<400> SEQUENCE: 5
ccgccgcgta ctgttct                                                  17

<210> SEQ ID NO 6
<211> LENGTH: 17
<212> TYPE: DNA
<213> ORGANISM: Haemophilus influenzae

<400> SEQUENCE: 6
ccatttgcta aaagtgc                                                  17
```

```
<210> SEQ ID NO 7
<211> LENGTH: 18
<212> TYPE: DNA
<213> ORGANISM: Haemophilus influenzae

<400> SEQUENCE: 7
ggaaaatcct gcagatgc                                              18

<210> SEQ ID NO 8
<211> LENGTH: 18
<212> TYPE: DNA
<213> ORGANISM: Haemophilus influenzae

<400> SEQUENCE: 8
aagcaacgta cggatgtg                                              18
```